(12) United States Patent
Hwang et al.

(10) Patent No.: US 7,915,012 B2
(45) Date of Patent: Mar. 29, 2011

(54) METHODS FOR SCREENING FOR INHIBITORS OF TRPV2 ACTIVATION

(75) Inventors: Sun Wook Hwang, Seoul (KR); Sang Soo Bang, Gwangmyeong-si (KR); Sang Heon Lee, Seoul (KR)

(73) Assignee: Korea University Industry and Academic Collaboration Foundation, Seoul (KR)

( * ) Notice: Subject to any disclaimer, the term of this patent is extended or adjusted under 35 U.S.C. 154(b) by 200 days.

(21) Appl. No.: 12/196,116

(22) Filed: Aug. 21, 2008

(65) Prior Publication Data

US 2009/0215107 A1    Aug. 27, 2009

(30) Foreign Application Priority Data

Feb. 25, 2008   (KR) .................. 10-2008-0016749

(51) Int. Cl.
*C12N 15/09* (2006.01)

(52) U.S. Cl. ...................................... 435/69.2

(58) Field of Classification Search .................. 435/69.2
See application file for complete search history.

(56) References Cited

U.S. PATENT DOCUMENTS

| 2009/0269280 A1 | 10/2009 | Hwang et al. |  |
| 2010/0137260 A1* | 6/2010 | Hwang et al. | 514/143 |

FOREIGN PATENT DOCUMENTS

| JP | 20072597 | 10/2007 |
| WO | 2007053526 | 10/2007 |

OTHER PUBLICATIONS

Behrendt H. et al. Characterization of the Mouse Cold Menthol Receptor TRPM8 . . . British J of Pharmacology 141(4)737-745, Feb. 2, 2004.*

Lee S. et al. Sensitization of Vanilloid Receptor Involves an Increase in the Phosphorylated Form of the Channel. Archives of Pharmacal Research 28(4)405-412, 2005.*

Hu H. et al. 2-Aminoethoxydiphenyl Borate is a Common Activator of TRPV1, TRPV2 and TRPV3. J of Biological Chemistry 279(34)35741-8, Aug. 20, 2004.*

Bang S. et al. "Transient receptor potential V2 expressed in sensory neurons is activated by probenecid"; (Aug. 24, 2007) *Neurosci.Lett.* 425(2):120-125.

Prosecution history for related application U.S. Appl. No. 12/109,256, 62 pp.

Andrade et al. (Apr. 25, 2006) "Contractile mechanisms coupled to TRPA1 receptor activation in rat urinary bladder" Biochem Pharmacol. 72(1):104-114.

Bandell et al. (Mar. 2004) "Noxious cold ion channel TRPA1 is activated by pungent compounds and bradykinin" Neuron. 41(6):849-857.

Bang et al. (Oct. 23, 2007) "Transient receptor potential A1 mediates acetaldehyde-evoked pain sensation" Eur. J. Neurosci. 26(9):2516-23.

Trevisani et al. (Aug. 7, 2007) "4-Hydroxynonenal, an endogenous aldehyde, causes pain and neurogenic inflamation through activation of the irritant receptor TRPA1" Proc. Natl. Acad. Sci. U.S.A. 104(33):13519-13524.

* cited by examiner

*Primary Examiner* — Ralph Gitomer

(74) *Attorney, Agent, or Firm* — Greenlee Sullivan P.C.

(57) ABSTRACT

The present invention relates to a method for activation of TRPV2 (transient receptor potential vanilloid 2) using probenecid, more precisely a method for selecting a candidate for TRPV2 blocker using probenecid. Probenecid of the present invention works on TRPV2 specifically so that it facilitates the isolation of sensory neurons expressing TRPV2. Therefore, probenecid of the invention can be effectively used for the studies on TRPV2 mechanisms and the development of a TRPV2 based anodyne.

11 Claims, 8 Drawing Sheets

[Fig. 1a]
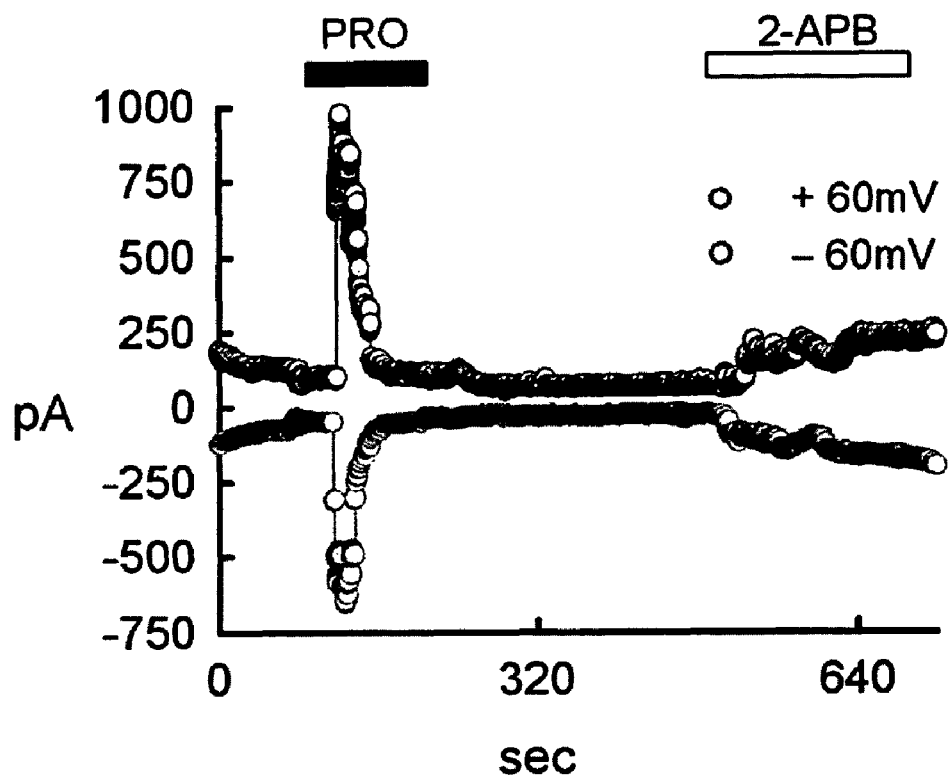
[Fig. 1b]
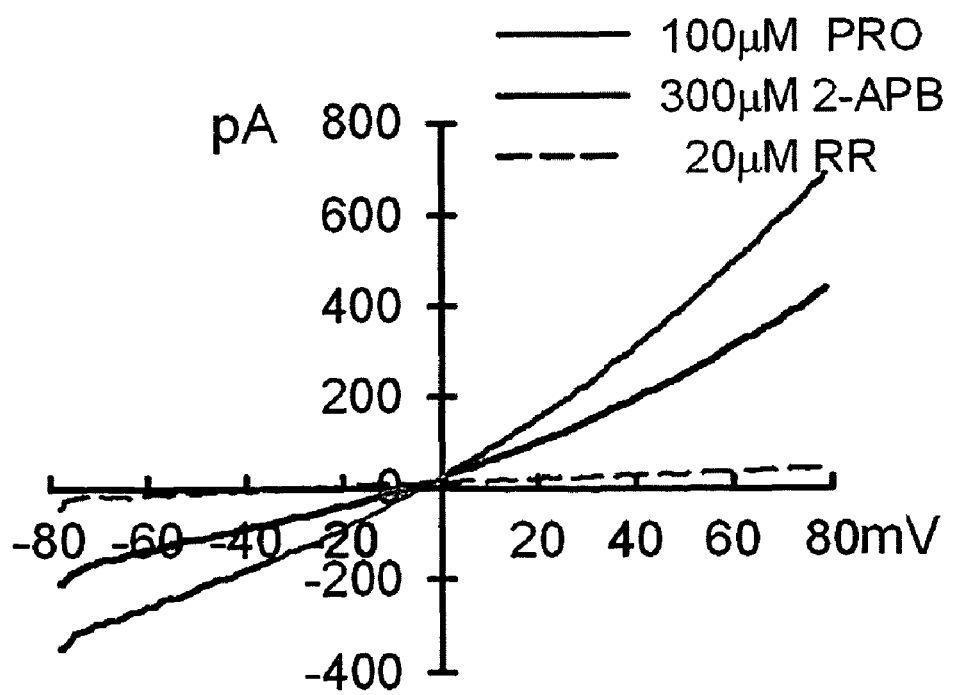

[Fig. 1c]
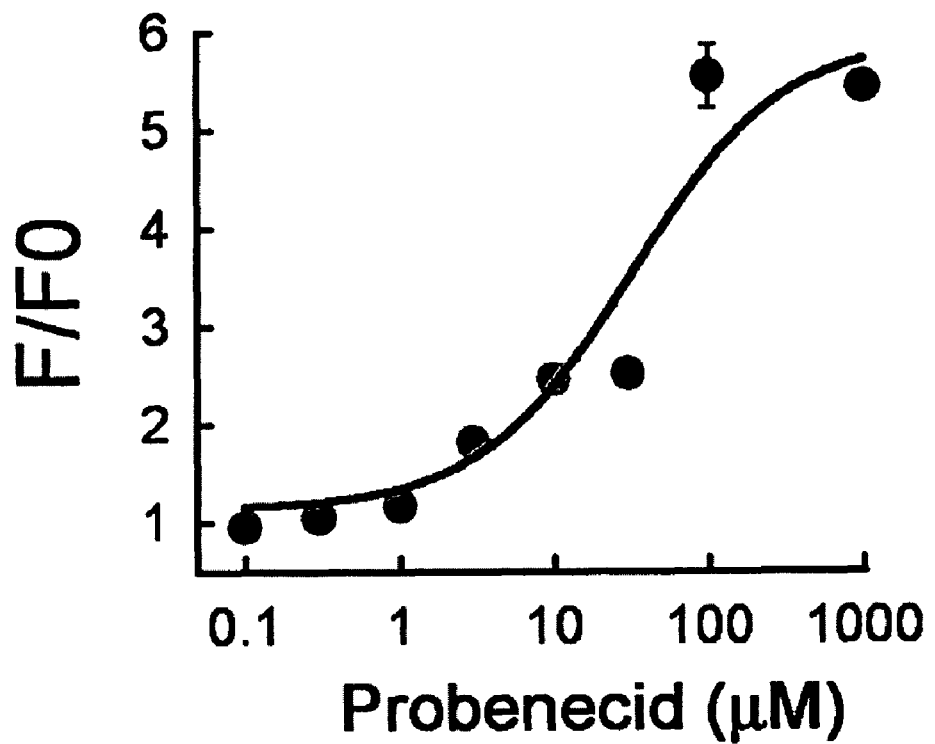
[Fig. 1d]
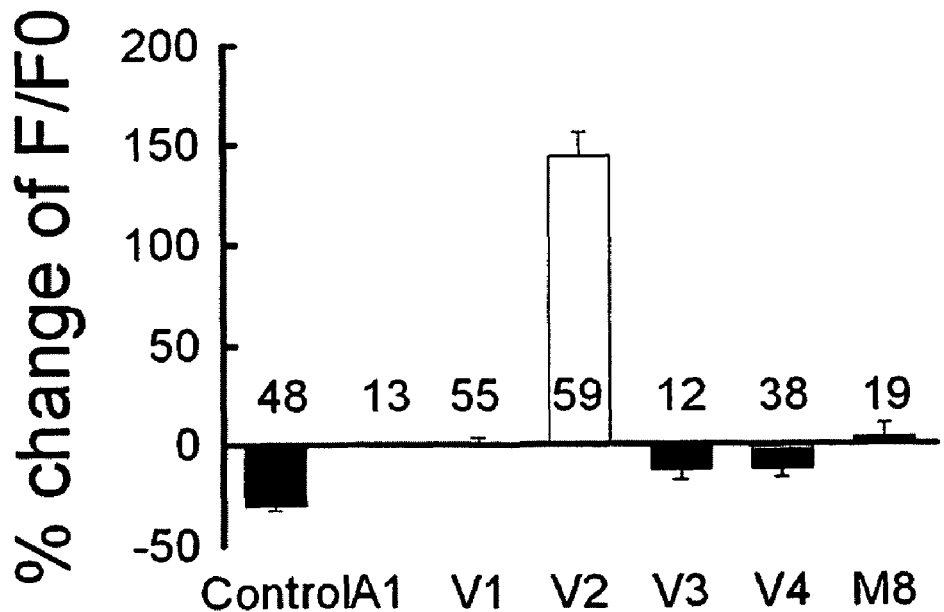

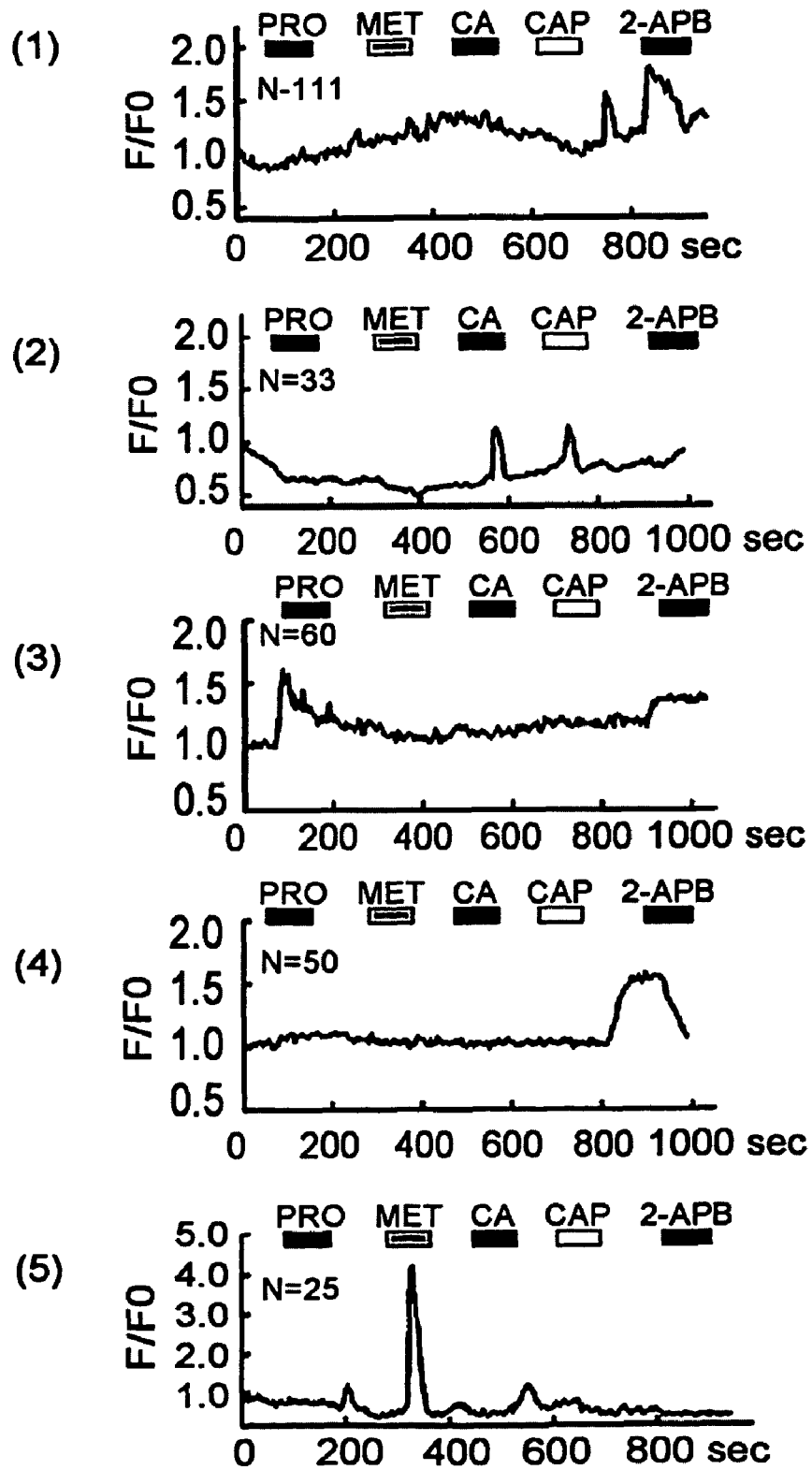

[Fig. 2b]
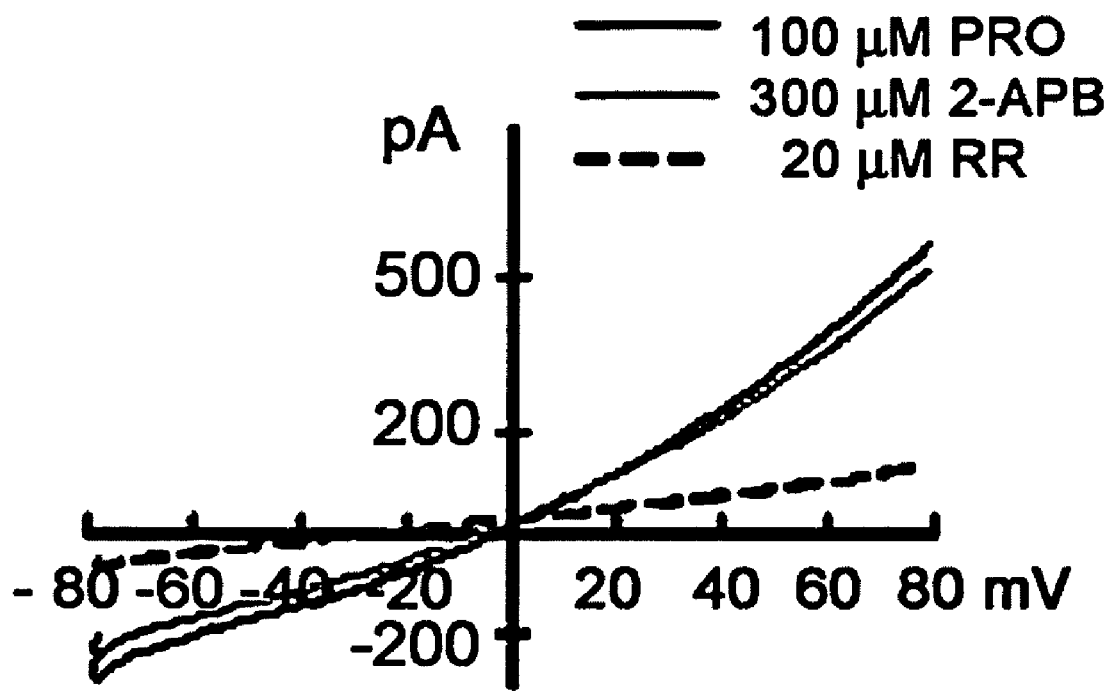
[Fig. 2c]
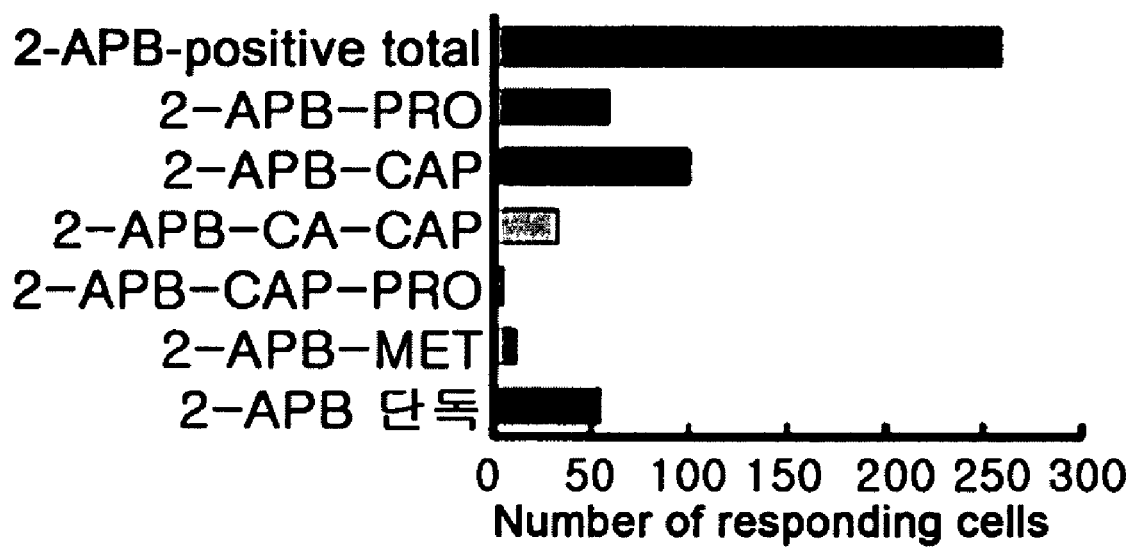

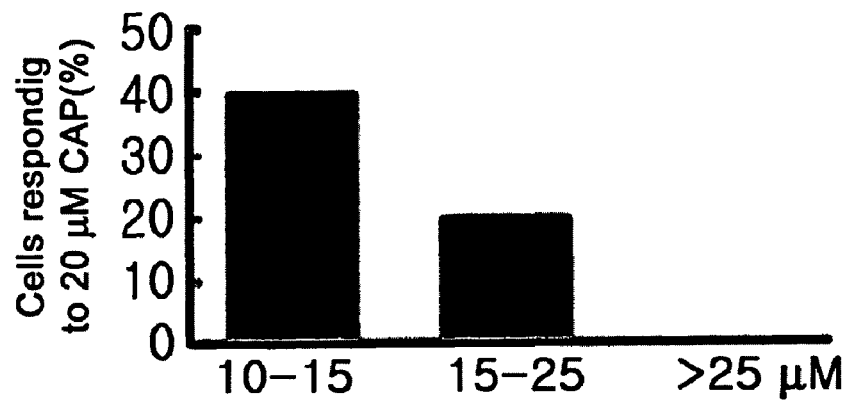
[Fig. 2d]
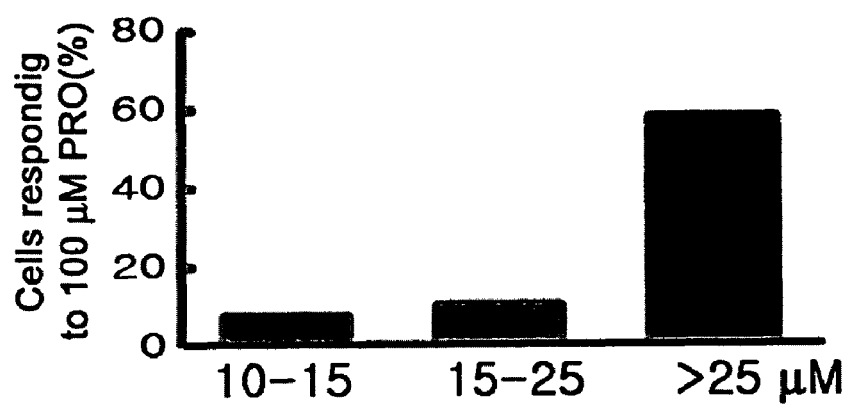
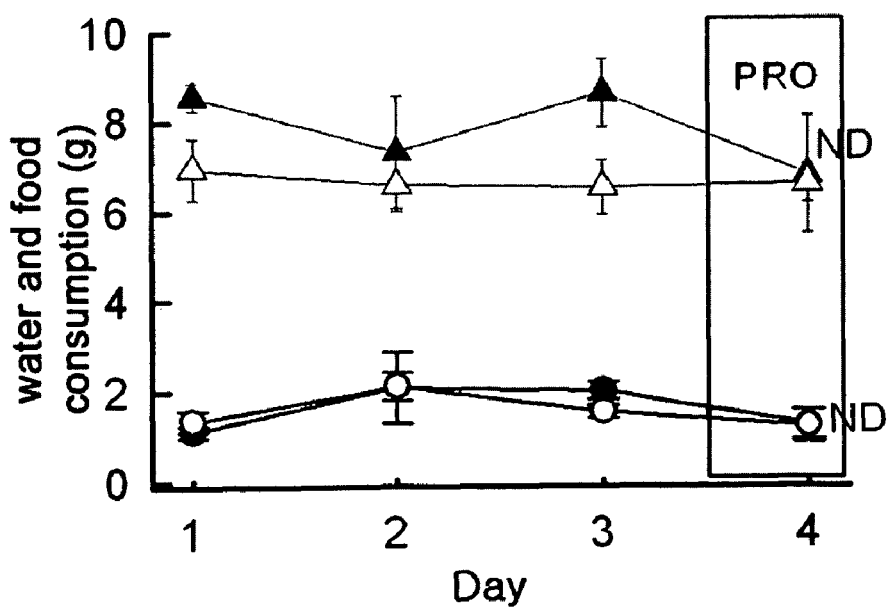
[Fig. 3a]

[Fig. 3b]
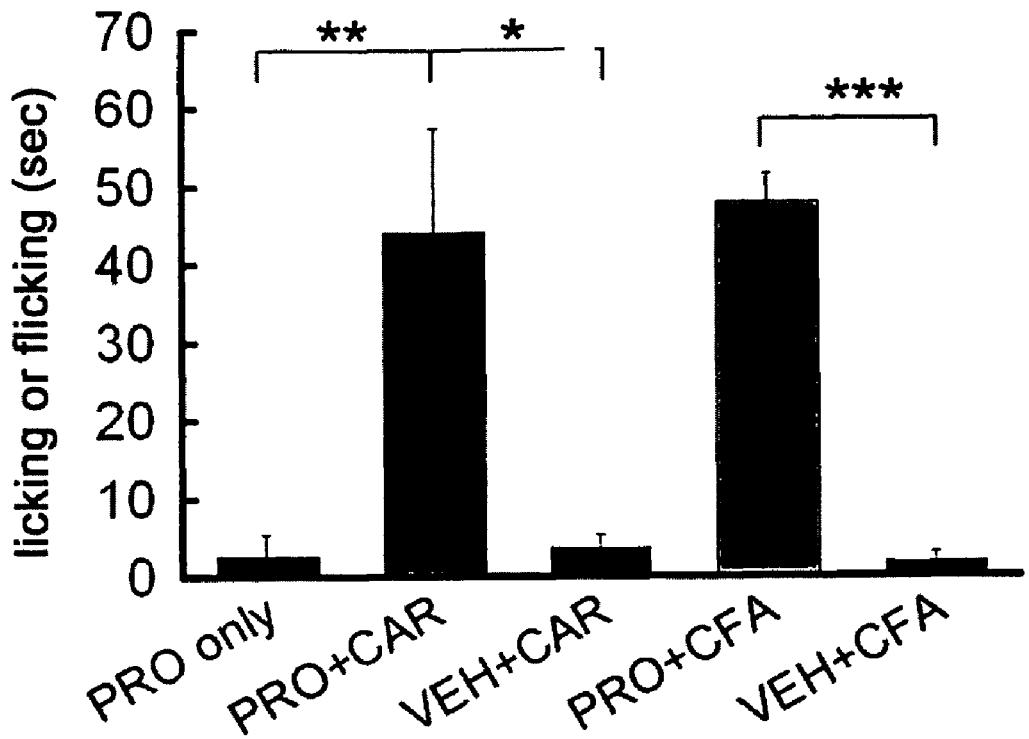
[Fig. 3c]
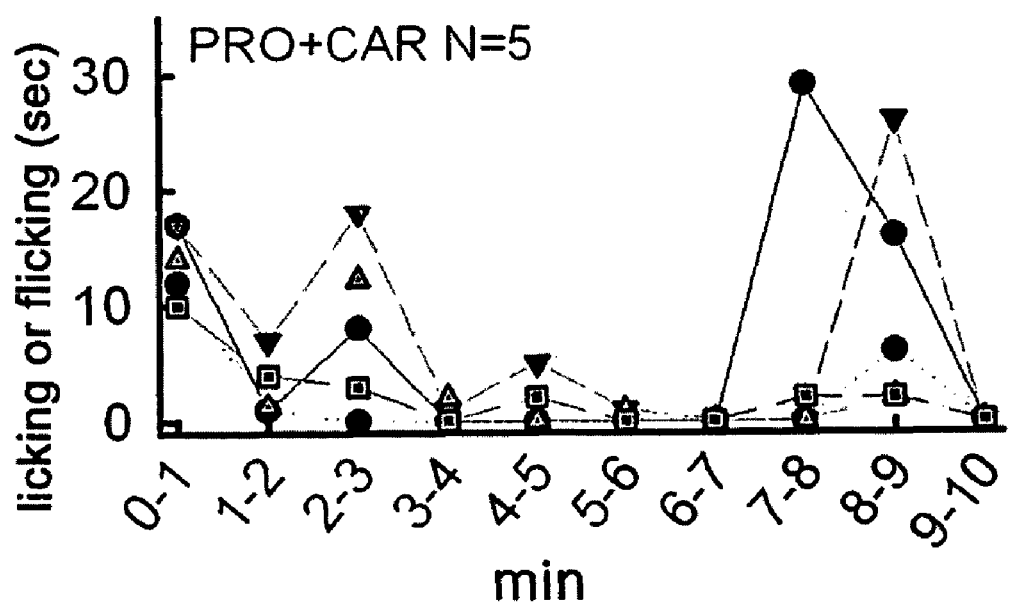

[Fig. 3d]
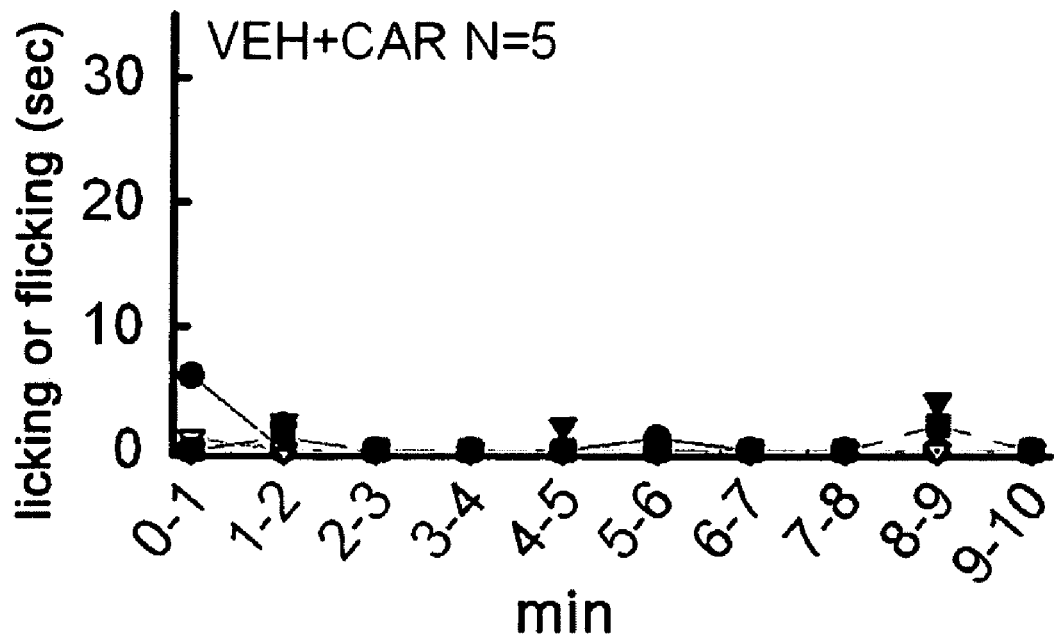
[Fig. 3e]
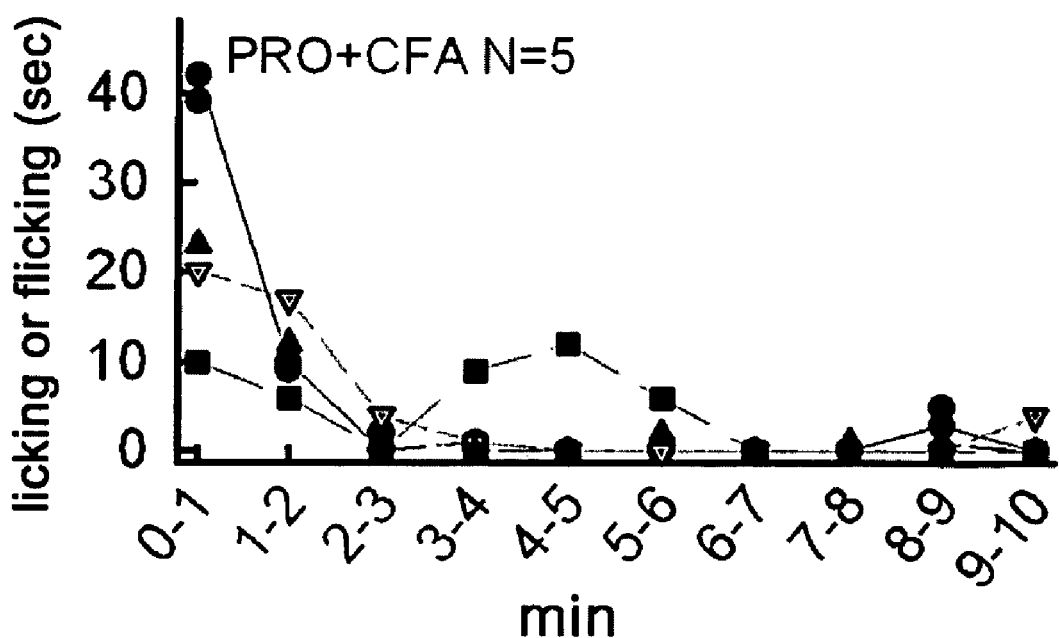

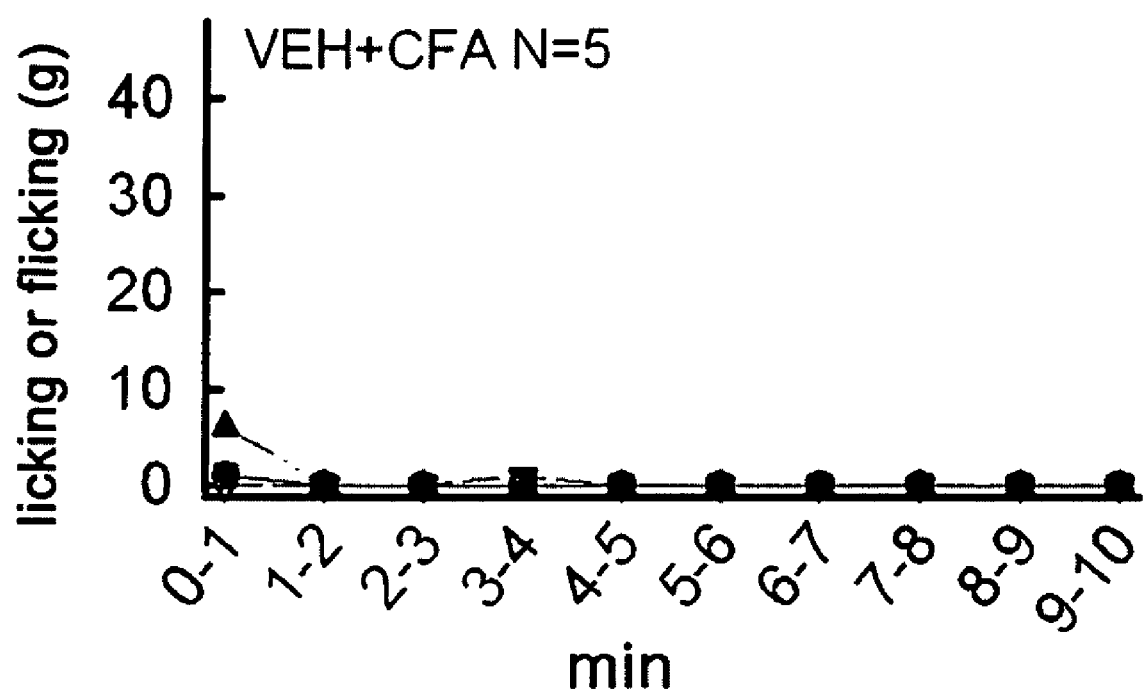
[Fig. 3f]

METHODS FOR SCREENING FOR INHIBITORS OF TRPV2 ACTIVATION

CROSS REFERENCE TO RELATED APPLICATIONS

This application claims priority under 35 U.S.C. 119 to Korean Patent Application 2008-10-0016749, filed Feb. 25, 2008.

TECHNICAL FIELD

The present invention relates to a method for activation of TRPV2 (transient receptor potential vanilloid 2) using probenecid.

BACKGROUND ART

Researchers in the field of human physiology and pharmacology found TRPV2 (transient receptor potential vanilloid 2) in human in 1999. TRPV2 was presumed to play an essential role in maintaining survival system in various tissues. In particular, TRPV2 is expressed in peripheral sensory nerve fibers which recognize pain. TRPV2 belongs to thermoTRP family (temperature-sensitive transient receptor potential ion channels) that is the pain receptor family recognizing temperature and painful stimuli. Many researchers expect that human pain mechanism will be disclosed by understanding the functions of TRPV2, the pain receptor, and finally the goal of relieving pain will be achieved by the development of a TRPV2 regulator. To examine TRPV2 functions and develop a TRPV2 regulator, a TRPV2 specific activator that only works for TRPV2 without affecting any other TRP receptors is required.

To understand basic techniques used for the development of a TRPV2 specific activator, it is important to understand the characteristics of TRPV2. TRPV2 is an ion channel and its activation makes cations migrate into sensory neurons, causing changes in membrane currents. The changes of membrane currents generate action potential signal and this potential signal is transmitted to the brain where pain is perceived. One of the techniques to measure TRPV2 activation is patch-clamp electrophysiological technique measuring the changes of membrane currents after amplifying thereof. And another technique to measure TRPV2 activation is to measure intracellular calcium level based on the fact that TRPV2 is involved in the migration of cations such as calcium ions. The first technique is superior in sensitivity to the second one, but the second technique is superior in high speed to the first one, so that they are complementary to each other. Such techniques to measure TRPV2 activation can be executed by the support of animal neuron culture technique, cell line culture technique, TRPV2 DNA control and transfection techniques. Various TRPV2 specific activator candidates are administered to TRPV2 over-expressing cells and then TRPV2 activation therein is measured to select a proper TRPV2 activator and determine its capacity.

A TRPV2 specific activator is an essential element to measure TRPV2 activation for further development of a TRPV2 regulator. However, no reports have been made so far in relation to a TRPV2 specific activator. The known TRPV2 activators are 2-APB (2-aminoethoxydiphenyl borate) and cannabinoid compounds. But, 2-APB is not specific to TRPV2 and in fact it can activate other TRP receptors such as TRPV1 and TRPV3, etc, suggesting that it is not very useful. In the meantime, cannabinoid compounds have their own cannabinoid receptor activation activity but have no specificity to TRPV2, making them not a good candidate for a TRPV2 specific activator.

Probenecid has been clinically used as a uricosuric agent for hyperuricemia which is a cause of gout and used to be co-treated with an antibiotic so as to inhibit the discharge of the antibiotic to increase the blood level of the antibiotic. The mechanism of probenecid based on the above two characteristics is to interrupt organic anion transporters carrying uric acid or antibiotics in the kidney. It has also been reported that probenecid interrupts such ion channel as CFTR (cystic fibrosis transmembrane conductance regulators). Such interrupting activities have nothing to do with the TRPV2 activation in sensory nerve.

Therefore, the present inventors constructed transformants expressing TRP and treated them with probenecid and other chemicals known as TRP activators, followed by comparison of the results. As a result, the inventors completed this invention by confirming that probenecid activated TRPV2 specifically and thus it can be effectively used for the screening of a TRPV2 activation blocker.

DISCLOSURE

Technical Problem

It is an object of the present invention to provide a method for screening a TRPV2 blocker using probenecid, the activator having TRPV2-specific activity.

Technical Solution

To achieve the above object, the present invention provides a method for activation of TRPV2 (transient receptor potential vanilloid 2) in vitro comprising the step of treating isolated neurons with probenecid.

The present invention also provides a method for isolating TRPV2 positive neurons comprising the following steps:
1) culturing the neurons isolated from a subject and treating them with probenecid;
2) measuring TRPV2 activity of the neurons treated in step 1); and,
3) selecting neurons which are positive to probenecid by comparing the TRPV2 activity measured in step 2) with the TRPV2 activity of neurons not treated with probenecid.

The present invention also provides a method for isolating TRPV2 negative neurons comprising the following steps:
1) culturing neurons isolated from a subject and treating them with probenecid and a non-specific TRPV2 activator stepwise in that order or in reverse order;
2) measuring the TRPV2 activity of the neurons treated in step 1); and
3) selecting neurons which are positive to the non-specific TRPV2 activator but negative to probenecid by comparing the TRPV2 activity measured in step 2) with that of the neurons not treated with probenecid and the non-specific TRPV2 activator, respectively.

The present invention also provides a method for screening a TRPV2 blocker comprising the following steps:
1) treating TRPV2 positive neurons with probenecid and TRPV2 blocker candidates;
2) treating TRPV2 negative neurons with the above TRPV2 blocker candidates and a non-specific TRPV2 activator;
3) measuring the TRPV2 activities of both TRPV2 positive neurons treated in step 1) and TRPV2 negative neurons treated in step 2); and 4) selecting candidates which inhibit TRPV2 activity of TRPV2 positive neurons treated with probenecid and TRPV2 blocker candidates but do not affect the TRPV2 activity of TRPV2 negative neurons treated with the TRPV2 blocker candidates and the non-specific TRPV2 activator by comparing the TRPV2 activity of step 3) with that of TRPV2 positive neurons treated with probenecid alone.

The present invention also provides a method for screening a TRPV2 blocker comprising the following steps:

1) constructing a transformant by transfecting a host cell with a plasmid containing polynucleotide encoding TRPV2;

2) treating the transformant with probenecid and TRPV2 blocker candidates;

3) treating TRPV2 negative neurons with the TRPV2 blocker candidates and a non-specific TRPV2 activator;

4) measuring the TRPV2 activities of both the transformant of step 2) and TRPV2 negative neurons of step 3); and, 5) selecting candidates which inhibit the TRPV2 activity of the transformant treated with probenecid and the TRPV2 blocker candidates but do not affect the TRPV2 activity of TRPV2 negative neurons treated with the TRPV2 blocker candidates and the non-specific TRPV2 activator by comparing each activity measured in step 4) with the TRPV2 activity of the transformant treated with probenecid alone.

In addition, the present invention also provides a method for screening a TRPV2 blocker comprising the following steps:

1) treating a subject with probenecid and TRPV2 blocker candidates;

2) measuring nociceptive behaviors induced in the subject treated in step 1); and, 3) selecting candidates inducing nociceptive behaviors by comparing the nociceptive behaviors measured in step 2) with those of the subject treated with probenecid alone.

Advantageous Effect

Probenecid of the present invention works on TRPV2 specifically so that it facilitates the isolation of sensory neurons expressing TRPV2. Therefore, probenecid of the invention can be effectively used for the studies on TRPV2 mechanisms and the development of a TRPV2 based anodyne.

DESCRIPTION OF DRAWINGS

The application of the preferred embodiments of the present invention is best understood with reference to the accompanying drawings, wherein:

FIG. 1 is a diagram illustrating the TRPV2 specific activity of probenecid (PRO: probenecid, RR: ruthenium red, A1: TRPA1, V1: TRPV1, V2: TRPV2, V3: TRPV3, V4: TRPV4, M8: TRPM8):

a: fast increase of whole cell current at +60 mV and −60 mV in HEK293T cells transformed with TRPV2 by the treatment of 100 µM probenecid (n=5);

b: current-voltage relation of TRPV2 responding by the treatment of 100 µM probenecid, 100 µM probenecid +20 µM ruthenium red and 300 µM 2-APB;

c: quantitative relation of TRPV2 activation with response to probenecid, determined by Fluo-3 calcium imaging; and, d: responses of different TRPs transformed cell lines to probenecid.

FIG. 2 is a diagram illustrating the responses of the mouse trigeminal neurons treated with a TRPV2 activator (MET: menthol, CA: cinnamaldehyde, CAP: capsaicin):

a: representative diagram illustrating the pharmacological response of neuron (N: number of each neuron);

1: capsaicin reactive neuron did not respond to probenecid;

2: capsaicin/cinnamaldehyde reactive neuron did not respond to probenecid;

3: 2-APB reactive neuron responded to probenecid;

4: 2-APB reactive neuron responded not to probenecid; and,

5: menthol reactive neuron did not respond to probenecid;

b: current-voltage relation of trigeminal neuron responding by the treatment of 100 µM probenecid, 100 µM probenecid +20 µM ruthenium red and 300 µM 2-APB;

c: composition of drug-sensitive neuron in 2-APB reactive neuron; and, d: distribution of cell body diameters of trigeminal neuron in which current response is induced by capsaicin or probenecid:

1: capsaicin-sensitive group; and,

2: probenecid-sensitive group.

FIG. 3 is a diagram illustrating that probenecid induces pain in inflammatory condition (VEH: vehicle, ND: no difference, CAR: carrageenan, CFA: complete Freund's adjuvant):

a: daily consumption of feed and water after the treatment with 20 mM probenecid (triangle: water consumption, circle: feed consumption, open symbols; probenecid treated group);

b: licking/flicking behavior of a rat observed for 10 minutes before the treatment of probenecid; and, c-f: time spent in licking/flicking behavior for 10 minutes after the treatment of various inflammation inducers:

c: carrageenan+25 µl of vehicle;

d: carrageenan+25 µl of vehicle+20 mM probenecid;

e: CFA+25 µl of vehicle; and, f: CFA+25 µl of vehicle +20 mM probenecid.

BEST MODE

Hereinafter, the present invention is described in detail.

The present invention provides a method for activation of TRPV2 (transient receptor potential vanilloid 2) in vitro comprising the step of treating isolated neurons with probenecid.

Probenecid stimulates the activation of TRPV2. In a preferred embodiment of the present invention, the effect of probenecid and 2-APB (2-aminoethoxydiphenyl borate) known as the conventional TRPV2 activator on TRPV2 was investigated by whole cell voltage clamp, a kind of patch clamp technique, and calcium imaging, a kind of technique to measure intracellular calcium level changes. As a result, the above two materials accelerated TRPV2 activation (see FIG. 1a) and this activation was inhibited by the conventional TRP pore blocker ruthenium red (see FIG. 1b). That is, every cell reacted to probenecid responded to 2-APB as well. Currents reacted to probenecid and 2-APB demonstrated outward rectifying which is one of typical characteristics of TRPV2-related currents.

Probenecid activates TRPV2 specifically. In a preferred embodiment of the present invention, activations of TRPA1 (transient receptor potential cation channel, subfamily A, member 1), TRPV1, TRPV3, TRPV4 and TRPVM8 (transient receptor potential cation channel, subfamily M, member 8), among TRPs known to be expressed in trigeminal neuron, induced by probenecid were examined in each transformed cell line. As a result, their activations were not confirmed (see FIG. 1d). The above result indicates that probenecid activates TRPV2 specifically.

In a preferred embodiment of the present invention, most of probenecid-induced calcium influx in trigeminal neurons was due to the response to 2-APB (see FIGS. 2a and 2c: 59 out of 60 neurons were responded) but not to the rest of chemical compounds. That is, trigeminal neuron demonstrated wide sensitivity to 2-APB (46.8% of the total neurons). Among neurons responding to capsaicin, a small group of neurons exhibiting sensitivity to probenecid was found (n=5 out of 111). 40.2% of the 2-APB sensitive group responded to capsaicin (presumably a TRPV1 expressing agent). The above results indicate that many neurons exhibiting increased calcium level by the treatment of 2-APB might have 2-APB sensitive component or TRPV3. The response pattern of the trigeminal neuron treated with a combined sensory organ chemical compound indicates that a small number of neurons form a probenecid reactant. In the meantime, probenecid-induced current in 2-APB-sensitive trigeminal neuron exhibited outward rectifying and was blocked by ruthenium red in whole cell voltage clamp experiment (see FIG. 2b).

Probenecid has TRPV2-specific activity. Therefore, it can be effectively used for the isolation of TRPV2 positive neurons from sensory neurons. It also helps to understand the mechanism of pain recognition by sensory neurons (ex. sensitivity to heat, chemical and mechanical stimuli) and facilitates the identification of diseases (ex. inflammatory pain, neuropathic pain and pain by adverse drug reaction). Probenecid can be administered to animals, followed by investigation of pain behaviors to confirm whether or not TRPV2 activation affected real behaviors. Thereby, among many pains, TRPV2-related pain could be distinguished. In addition, it can also be effectively used for the development of TRPV2 blockers. In the case that probenecid is used for the development of a TRPV2 activator, it can be used as the standard material for TRPV2 activator candidates. In the case that probenecid is used for the development of a TRPV2 blocker, it can be used to confirm whether or not the candidate could interrupt the activation of TRPV2 by probenecid. Probenecid is the only TRPV2 specific activator so far, so that it can be further modified as an enhanced activator or blocker by chemical processing.

The present invention also provides a method for isolating TRPV2 positive neurons comprising the following steps:
1) culturing the neurons isolated from a subject and treating them with probenecid;
2) measuring TRPV2 activity of the neurons treated in step 1); and,
3) selecting neurons which are positive to probenecid by comparing the TRPV2 activity measured in step 2) with the TRPV2 activity of neurons not treated with probenecid.

In a preferred embodiment of the invention, it was confirmed that there are probenecid specific responses in trigeminal neuron by pharmacological test and current-voltage profiling (see FIGS. 2a-2c). At least 70% of probenecid sensitive neurons (see FIG. 2d-2) were found in those neurons having a larger diameter (>25 µm in cell body diameter), which was consistent with the previous reports. Therefore, trigeminal neuron size analysis, pharmacological tests and current-voltage profiling all confirmed that probenecid is useful for the selection of a TRPV2 activator and blocker, and the novel TRPV2 activator probenecid was confirmed to be effective in isolation of TRPV2-positive neurons.

The subjects herein are vertebrates and preferably mammals and more preferably such test animals as rats, rabbits, guinea pigs, hamsters, dogs and cats, and most preferably apes such as chimpanzees and gorillas. The preferable concentration of probenecid of step 1) is 10-1000 µM.

In addition, the measuring TRPV2 activity in step 2) can be performed by whole-cell voltage-clamp recording measuring the changes of membrane currents by amplifying thereof or calcium imaging measuring intracellular calcium level changes based on the founding that TRPV2 is able to move cations such as calcium ions, but not always limited thereto.

The present invention also provides a method for isolating TRAP2 negative neurons comprising the following steps:
1) culturing neurons isolated from a subject and treating them with probenecid and a non-specific TRPV2 activator stepwise in that order or in reverse order;
2) measuring the TRPV2 activity of the neurons treated in step 1); and
3) selecting neurons which are positive to the non-specific TRPV2 activator but negative to probenecid by comparing the TRPV2 activity measured in step 2) with that of the neurons not treated with probenecid and the non-specific TRPV2 activator, respectively.

The TRPV2 non-specific activator in step 1) is preferably one of the activators of thermoTRP group (temperature-sensitive transient receptor potential ion channels) including TRPV2 such as 2-APB (2-Aminoethoxydiphenyl borate), capsaicin, cinnamaldehyde or menthol, but not always limited thereto.

In addition, the measuring TRPV2 activity in step 2) can be performed by whole-cell voltage-clamp recording or calcium imaging measuring intracellular calcium level changes, but not always limited thereto.

The present invention also provides a method for screening a TRPV2 blocker comprising the following steps:
1) treating TRPV2 positive neurons with probenecid and TRPV2 blocker candidates;
2) treating TRPV2 negative neurons with the above TRPV2 blocker candidates and a non-specific TRPV2 activator;
3) measuring the TRPV2 activities of both TRPV2 positive neurons treated in step 1) and TRPV2 negative neurons treated in step 2); and
4) selecting candidates which inhibit TRPV2 activity of TRPV2 positive neurons treated with probenecid and TRPV2 blocker candidates but do not affect the TRPV2 activity of TRPV2 negative neurons treated with the TRPV2 blocker candidates and the non-specific TRPV2 activator by comparing the TRPV2 activity of step 3) with that of TRPV2 positive neurons treated with probenecid alone.

The TRPV2 positive neurons and the TRPV2 negative neurons are characteristically isolated by the method of the present invention. The candidates of step 1) are selected from the group consisting of natural compounds, synthetic compounds, RNA, DNA, polypeptides, enzymes, proteins, ligands, antibodies, antigens, metabolites of bacteria or fungi and bioactive molecules, but not always limited thereto.

The present invention also provides a method for screening a TRPV2 blocker comprising the following steps:
1) constructing a transformant by transfecting a host cell with a plasmid containing polynucleotide encoding TRPV2;
2) treating the transformant with probenecid and TRPV2 blocker candidates;
3) treating TRPV2 negative neurons with the TRPV2 blocker candidates and a non-specific TRPV2 activator;
4) measuring the TRPV2 activities of both the transformant of step 2) and TRPV2 negative neurons of step 3); and,
5) selecting candidates which inhibit the TRPV2 activity of the transformant treated with probenecid and the TRPV2 blocker candidates but do not affect the TRPV2 activity of TRPV2 negative neurons treated with the TRPV2 blocker candidates and the non-specific TRPV2 activator by comparing each activity measured in step 4) with the TRPV2 activity of the transformant treated with probenecid alone.

The host cell herein is preferably the one that is useful for the studies on calcium channel activity and high throughput blocker screening, which is exemplified by HEK cell line, CHO cell line, HeLa cell line, and RBL-2H3 cell line, but not always limited thereto.

Probenecid of step 2) activates TRPV2 specifically. THC (delta9-tetrahydrocannabinol) and 2-APB have been known to activate TRPV2, but their activities are not TRPV2 specific. That is, THC activates TRPA1 as well and 2-APB activates TRPV1 and TRPV3 altogether.

In a preferred embodiment of the present invention, among TRPs known to be expressed in sensory neurons, only TRPV2 showed a remarkable sensitivity to probenecid in terms of its activation (see FIG. 1d). The preferable concentration of probenecid is 10-1000 μM. In a preferred embodiment of the present invention, the EC50 (effective concentration 50%) of probenecid on TRPV2 was 31.9 μM, and the maximal effective dose was about 1 mM. This suggests that probenecid exerted an action on the TRPV2 activity throughout the micromolar ranges(see FIG. 1c).

In addition, the present invention also provides a method for screening a TRPV2 blocker comprising the following steps:

1) treating a subject with probenecid and TRPV2 blocker candidates;
2) measuring nociceptive behaviors induced in the subject treated in step 1); and,
3) selecting candidates inducing nociceptive behaviors by comparing the nociceptive behaviors measured in step 2) with those of the subject treated with probenecid alone.

TRPV2 is required by pain sensor expressed in thinly myelinated nociceptors. In a preferred embodiment of the present invention, it was investigated whether or not nocifensive behavior was induced by the treatment of probenecid. First, an oral aversion test was performed and as a result, the administration of probenecid did not induce oral aversion that could affect water or feed consumption (see FIG. 3a). Then, probenecid was administered to mice with inflammation induced by carrageenan or CFA on the hind paws. As a result, the mouse group treated with probenecid demonstrated significantly extended behavior time, while the group treated with vehicle alone without probenecid did not exhibit behavial response (see FIGS. 3b-3f).

The subjects herein are vertebrates and preferably mammals and more preferably mammals except human and more than preferably such test animals as rats, rabbits, guinea pigs, hamsters, dogs and cats, and most preferably apes such as chimpanzees and gorillas. The preferable concentration of probenecid of step 1) is 10-100 mM. In step 1), the administration is performed by parenteral administration and preferably by intradermal injection, but not always limited thereto. In step 2), the investigation on nociceptive behaviors is preferably performed by analyzing hindpaw licking/flicking behaviors, but not always limited thereto. The inflammatory sensitization can be induced by the injection of carrageenan or CFA (complete Freund's adjuvant) before the administration of probenecid.

Mode for Invention

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Construction of cell lines transfected with TRPV

HEK293T cell line (ATCC CRL-1 1268) was transiently transfected with plasmid DNA containing polynucleotide encoding rTRPA1 (SEQ. ID. NO: 1), rTRPV2 (SEQ. ID. NO: 2), mTRPV3 (SEQ. ID. NO: 3), rTRPV4 (SEQ. ID. NO: 4), mTRPM8 (SEQ. ID. NO: 5) or mTRPA1 (SEQ. ID. NO: 6).

Particularly, the HEK293T cell line was transiently transfected with individual TRP channel plasmid (pcDNA3.1 containing polynucleotide encoding rTRPV1, rTRPV2, mTRPV3, rTRPV4, mTRPM8 or mTRPA1), and 600 ng/well of pCDNA3 (Invitrogen Corp., USA; containing green fluorescent protein (GFP) cDNA) using Fugene6 (Roche Diagnostics, USA) according to manufacturer's instruction. The transformed cells were cultured in DMEM/F12 containing 10% FBS and 1% penicillin/streptomycin in a $CO_2$ incubator for 24 hours. The cells were replated onto poly-L-lysine-coated glass coverslips, followed by further culture for 10-24 hours.

EXAMPLE 2

Preparation of trigeminal neurons

Trigeminal ganglia were dissected out of decapitated adult ICR mice in cold PBS and treated with 1.5 mg/ml of collagenase/dispase (Roche Diagnostics, USA) at 37° for 45 min, and then treated with 0.25% trypsin (Invitrogen, USA) for 15 min. The trigeminal neurons prepared thereby were then plated onto poly-L-lysinecoated coverslips in DMEM/F12 containing 10% FBS, 1% penicillin/streptomycin and 5 ng/ml of 2.5S NGF (Invitrogen, USA), followed by culture in a $CO_2$ incubator for 48-72 hours.

EXPERIMENTAL EXAMPLE 1

Investigation of TRPV2 activation by probenecid or 2-APB (2-aminoethoxydiphenyl borate)

<1-1>Treatment with of probenecid and 2-APB

The TRPV2 transfected cell line prepared in Example 1 was treated with 100 μM probenecid (Sigma-Aldrich, USA) and 300 μM 2-APB (2-aminoethoxydiphenyl borate; Cayman Chemical, USA), respectively. Stock solutions were made using water, DMSO or ethanol, and were diluted with test solutions before use.

<1-2> Whole-Cell Voltage-Clamp Experiment

Whole-cell voltage-clamp recording, one of the patch-clamp techniques, was performed with the transfected cell line of Example <1-1> according to the method of Bandel M, et al. (Neuron 41:849-857, 2004).

Particularly, the extracellular solution (140 mM NaCl, 5 mM KCl, 2 mM $CaCl_2$, 1 mM $MgCl_2$, 10 mM HEPES; titrated to pH 7.4 with NaOH) and the pipette solution (140 mM CsCl, 5 mM EGTA, 10 mM HEPES, 2.0 mM MgATP, 0.2 mM NaGTP; titrated to pH 7.2 with CsOH) were used. The potential was held at −60 mV for 250 ms, voltage-ramp pulsed from −80 mV to +80 mV for 325 seconds and returned to −60 mV for 250 ms, which was repeated without inter-sweep. This experiment was repeated 5 times.

As a result, as shown in FIG. 1a, as soon as probenecid was added, a significant increase of current was observed. The cells exhibited equal response by the treatment of 2-APB known as a TRPV2 activator (FIG. 1a). That is, every cell responding to probenecid responded to 2-APB. Currents reacted to probenecid and 2-APB demonstrated outward rectifying which is one of typical characteristics of TRPV2-related currents.

EXPERIMENTAL EXAMPLE 2

Investigation of block of TRPV2 activation by probenecid or 2-APB using ruthenium red The TRPV2 transfected cell line prepared by the method of Example 1 was treated with 100 μM probenecid, 100 μM probenecid+20 μM ruthenium red (Sigma-Aldrich, USA) and 300 μM 2-APB, respectively. Stock solutions were made using water, DMSO or ethanol, and were diluted with test solutions before use. Then, whole-cell voltage-clamp recording was performed by the same manner as described in Experimental Example <1-2>.

As a result, as shown in FIG. 1b, probenecid induced response shown in FIG. 1a was inhibited by ruthenium red, a general TRP pore blocker.

EXPERIMENTAL EXAMPLE 3

Probenecid specific and dose-dependent response of TRPV2

<3-1> Treatment of Probenecid and 2-APB

The TRPV2 transfected cell line prepared in Example 1 was treated with 100 μM probenecid and 300 μM 2-APB.

<3-2> Treatment of Probenecid at Different Concentrations

The TRPV2 transfected cell line prepared in Example 1 was treated with probenecid at different concentrations from 0.1 to 1,000 μM.

<3-3> Measurement of Intracellular Calcium Level Changes by Calcium Imaging

Calcium imaging was performed with the transfected cell lines treated as above.

Particularly, the transfected cell line of Example <3-1> and Example <3-2> was loaded with Fluo-3AM (5 μM; Sigma Aldrich, USA) in the bath solution (140 mM NaCl, 5 mM KCl, 2 mM $CaCl_2$, 1 mM $MgCl_2$, 10 mM HEPES; adjusted to pH 7.4 with NaOH) containing 0.02% pluronic acid (Invitrogen, USA) at 37° C. for 1 hour. Calcium imaging was performed with a confocal microscope (LSM5 Pascal, Carl Zeiss, Germany), and time-lapse images (excitation 488 nm/emission 514 nm) were collected every 3 seconds using Carl Zeiss ratio tool software (Carl Zeiss, Germany). Mean value curve of calcium influx responses (n=12–62 per each experimental values) was made by Hill plot (Kd: 31.9 μM, n: 2.8).

As a result, TRPV2-specific reaction was detected by Fluo-3 calcium imaging (n=59), as shown in FIG. 1a.

As shown in FIG. 1c, the $EC_{50}$ (effective concentration 50%) of probenecid on TRPV2 was 31.9 μM, and the maximal effective dose was about 1 mM. This suggests that probenecid exerted an action on the TRPV2 activity throughout the micromolar ranges.

EXPERIMENTAL EXAMPLE 4

Investigation of responses to probenecid in different TRP transfected cell lines The TRPA1, TRPV1, TRPV2, TRPV3, TRPV4 and TRPM8 transfected cell lines prepared by the method of Example 1 and the non-transfected HEK cell line (control group) were treated with 100 μM probenecid. Calcium imaging was performed with the transfected cell lines treated as the above by the same manner as described in Example <3-3>.

As a result, as shown in FIG. 1d, among 6 TRPs known to be expressed in trigeminal neurons, only TRPV2 was activated by probenecid.

EXPERIMENTAL EXAMPLE 5

Investigation of probenecid responses in trigeminal neurons

The trigeminal neurons prepared by the same manner as described in Example 2 were delayed-treated with 100 μM probenecid or 4 kinds of TRP activators: TRPM8 activator menthol 400 μM, TRPA1 activator cinnamaldehyde (MP Biomedicals, USA) 300 μM, TRPV1 activator capsaicin (Sigma-Aldrich, USA) 2 μM and TRPV1-3 activator 2-APB 300 μM. Calcium imaging was performed with the trigeminal neurons treated as the above by the same manner as described in Example <3-3>.

As a result, as shown in FIG. 2a, a neuron group with calcium influx induced as a response to probenecid was found. That is, 2-APB reactive neurons responded to probenecid as well (FIGS. 2a-3 and 4). However, major capsaicin-sensitive neuron groups (FIG. 2a-1) and all capsaicin/cinnamaldehyde-sensitive neuron groups (FIG. 2a-2), regarded as TRPV1/TRPA1 co-expressers, did not exhibit probenecid induced intracellular calcium influx. In the meantime, menthol-reactive TRPM8 positive neurons did not respond to probenecid (FIG. 2a-5).

EXPERIMENTAL EXAMPLE 6

Inhibition of response to probenecid or 2-APB by ruthenium red in trigeminal neurons The trigeminal neurons prepared by the same manner as described in Example 2 were treated with 100 μM probenecid, 100 μM probenecid+20 μM ruthenium red and 300 μM 2-APB, respectively. Then, whole-cell voltage-clamp recording was performed by the same manner as described in Experimental Example <1-2>.

As a result, as shown in FIG. 2b, probenecid induced currents exhibited outward rectifying in 2-APB-sensitive trigeminal neurons, which were inhibited by ruthenium red, confirmed by whole cell voltage clamp experiment.

EXPERIMENTAL EXAMPLE 7

Response to probenecid or 2-APB in trigeminal neurons

The trigeminal neurons prepared by the same manner as described in Example 2 were treated with 300 μM 2-APB+100 μM probenecid, 300 μM 2-APB+2 μM capsaicin, 300 μM 2-APB+300 μM cinnamaldehyde+2 μM capsaicin, 300 μM 2-APB +2 μM capsaicin +100 μM probenecid, 300 μM 2-APB +400 μM menthol and 300 μM 2-APB, respectively. Then, calcium imaging was performed by the same manner as described in Experimental Example <3-3>.

As a result, as shown in FIG. 2c, most of probenecid-induced calcium influx in neurons was due to the response to 2-APB (59 out of 60 neurons were responded). That is, trigeminal neurons demonstrated wide sensitivity to 2-APB (46.8% of the total neurons). Among neurons responding to capsaicin, a small group of neurons exhibiting sensitivity to probenecid was found (n=5 out of 111). 40.2% of the 2-APBsensitive group responded to capsaicin (presumably a TRPV1 expressing agent). The above results indicate that many neurons exhibiting increased calcium level by the treatment of 2-APB might have 2-APB sensitive component or TRPV3. 7.7% of probenecid-sensitive neurons responded to capsaicin, and 3.5% of capsaicin-sensitive neurons responded to probenecid. The response pattern of the trigeminal neurons treated with a combined sensory organ chemical compound indicated that a small number of neurons formed a probenecid reactant. All the neurons were in medium sizes and n=5.

EXPERIMENTAL EXAMPLE 8

Measurement of the size of probenecid-sensitive neuron

The size of probenecid-sensitive neuron cell body was measured by a scale of microscope and a scale ruler, and the ratio of responding neurons to the entire neurons was calculated over the sizes.

As a result, as shown in FIG. 2d, at least 70% of probenecid-sensitive neurons (FIG. 2d-2) had wider diameter (>25 μm in cell body diameter). In the meantime, capsaicin-sensitive neurons (FIG. 2d-1) were in small-medium sizes (10-25 μm). TRPV2 expressing neurons were largely those in medium-large sizes, and this observation by the present inventors was consistent with the previous reports.

EXPERIMENTAL EXAMPLE 9

Oral aversion test

Oral aversion test was confirmed according to the methods of Caterina M J, et al. (*Science* 288:306-313, 2000) and Kwan K Y, et al. (*Neuron* 50: 277-289, 2006).

Particularly, adult ICR mice randomly selected and raised were allowed to drink water containing 0.125% saccharin (Sigma Aldrich, USA) only for three hours a day. Water and feed were provided for 4 days. Water and feed consumptions were measured everyday. On day 4, water containing 20 mM probenecid was provided for 3 hours. Statistical data were analyzed by two-tailed, unpaired Student's-t-test and the results were presented by mean ±S.E.M.

As a result, as shown in FIG. 3a, there was no significant difference between the group treated with probenecid and the group not treated with probenecid (n=5), and there was no difference in water and feed consumption rates between 3 days before the treatment of probenecid and after the treatment of water containing probenecid (20 mM). The above result indicates that the probenecid treatment did not induce oral aversion showing avoidance of water or feed.

EXPERIMENTAL EXAMPLE 10

Licking/flicking behaviors

<10-1> Inducement of inflammatory sensitization

Inflammatory sensitization by probenecid was investigated. Particularly, 50 μl of 1% carrageenan (Sigma Aldrich, USA) was injected to the right hind paws of mice 3 hours before the probenecid injection or 50 μl of CFA (complete Freund's adjuvant; Sigma Aldrich, USA) was injected 24 hours before the probenecid injection. Before the experiment, the mice were adapted for one hour to the experimental environment. 25 Ml of vehicle (saline containing 3% DMSO and 0.5% Tween 80) alone or 25 Ml of vehicle containing probenecid (20 mM) was injected to the right hind paws of the mice.

<10-2> Investigation of Acute Licking/Flicking Behaviors

The time spent for the hindpaw licking/flicking behaviors in mice were measured according to the method of Bandell M, et al. (*Neuron* 41:849-857, 2004) and Moqrich A, et al. (*Science* 307:1468-1472, 2005), for 10 minutes. Statistical data were analyzed by two-tailed, unpaired Student's-t-test and the results were presented by mean ±S.E.M. (*$p<0.001$, $p<0.01$, *$p<0.05$ and ND, $p>0.05$).

As a result, after the probenecid injection to the hind paws of mice, there were no significant changes in behavior in normal mice. However, in the mice with inflammation induced locally by carrageenan (for three hours) or CFA (for one day), behavial changes were observed over the time (FIGS. 3b, 3c and 3e). The mice treated with vehicle alone did not show any changes (FIGS. 3b, 3d and 3f). The above results indicate that probenecid can induce pain in a specific inflammatory condition.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for screening a TRPV2 (transient receptor potential vanilloid 2) blocker comprising the following steps:
   1) treating TRPV2 positive neurons with probenecid and TRPV2 blocker candidates;
   2) treating TRPV2 negative neurons with the TRPV2 blocker candidates of step 1) and a non-specific TRPV2 activator;
   3) measuring TRPV2 activities of both TRPV2 positive neurons treated in step 1) and TRPV2 negative neurons treated in step 2); and
   4) selecting candidates which inhibit TRPV2 activity of TRPV2 positive neurons treated with probenecid and TRPV2 blocker candidates but do not affect the TRPV2 activities of TRPV2 negative neurons treated with the TRPV2 blocker candidates and the non-specific TRPV2 activator by comparing the TRPV2 activities of step 3) with that of TRPV2 positive neurons treated with probenecid alone.

2. The method for screening according to claim 1, wherein the TRPV2 positive neurons are isolated by a method comprising the following steps:
   1) culturing the neurons isolated from a subject and treating them with probenecid;
   2) measuring TRPV2 activity of the neurons treated in step 1); and,
   3) selecting neurons which are positive to probenecid by comparing the TRPV2 activity measured in step 2) with the TRPV2 activity of neurons not treated with probenecid.

3. The method for screening according to claim 1, wherein the TRPV2 negative neurons are isolated by a method comprising the following steps:

1) culturing neurons isolated from a subject and treating them with probenecid and a non-specific TRPV2 activator stepwise in the order set forth in claim 1 or in reverse order;
2) measuring the TRPV2 activity of the neurons treated in step 1); and
3) selecting neurons which are positive to the non-specific TRPV2 activator but negative to probenecid by comparing the TRPV2 activity measured in step 2) with that of the neurons not treated with probenecid and the non-specific TRPV2 activator, respectively.

4. The method for screening according to claim 1, wherein the TRPV2 positive neurons are treated with probenecid in step 1) at a concentration from 10-1000 μM.

5. The method for screening according to claim 1, wherein the non-specific TRPV2 activator of step 2) is selected from the group consisting of 2-APB, capsaicin, cinnamaldehyde and menthol.

6. The method for screening according to claim 1, wherein the measuring of TRPV2 activity in step 3) is performed by whole-cell voltage-clamp technique or calcium imaging.

7. A method for screening a TRPV2 blocker comprising the following steps:
1) constructing a transformant by transfecting a host cell with a plasmid treating the transformant;
2) treating the transformant of step 1) with probenecid and TRPV2 blocker candidates;
3) treating TRPV2 negative neurons with the TRPV2 blocker candidates of step 2) and a non-specific TRPV2 activator;
4) treating the transformant of step 1) with probenecid alone;
5) measuring TRPV2 activities of both the transformant of step 2) and TRPV2 negative neurons of step 3); and,
6) selecting candidates which inhibit the TRPV2 activity of the transformant treated with probenecid and the TRPV2 blocker candidates but do not affect the TRPV2 activity of TRPV2 negative neurons treated with the TRPV2 blocker candidates and the non-specific TRPV2 activator by comparing each activity measured in step 4) with the TRPV2 activity of the transformant treated with probenecid alone.

8. The method for screening according to claim 7, wherein the TRPV2 negative neurons are isolated by a method comprising the following steps:
1) culturing neurons isolated from a subject and treating them with probenecid and a non-specific TRPV2 activator stepwise in the order set forth in claim 7 or in reverse order;
2) measuring TRPV2 activity of the neurons treated in step 1); and
3) selecting neurons which are positive to the non-specific TRPV2 activator but negative to probenecid by comparing the TRPV2 activity measured in step 2) with that of the neurons not treated with probenecid and the non-specific TRPV2 activator, respectively.

9. The method for screening according to claim 7, wherein the transformant is treated with probenecid in step 2) at a concentration of 10-1000 μM.

10. The method for screening according to claim 7, wherein the non-specific TRPV2 activator of step 3) is selected from the group consisting of 2-APB, capsaicin, cinnamaldehyde and menthol.

11. The method for screening according to claim 7, wherein the measuring of TRPV2 activity in step 5) is performed by whole-cell voltage-clamp technique or calcium imaging.

\* \* \* \* \*

UNITED STATES PATENT AND TRADEMARK OFFICE
CERTIFICATE OF CORRECTION

| | | |
|---|---|---|
| PATENT NO. | : 7,915,012 B2 | Page 1 of 1 |
| APPLICATION NO. | : 12/196116 | |
| DATED | : March 29, 2011 | |
| INVENTOR(S) | : Sun Wook Hwang, Sang Soo Bang and Sang Heon Lee | |

It is certified that error appears in the above-identified patent and that said Letters Patent is hereby corrected as shown below:

In claim 7, line 2 of subparagraph 1), "treating the transformant;" should be replaced with --containing polynucleotide encoding TRPV2;--.

Signed and Sealed this
Thirty-first Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,915,012 B2 | Page 1 of 1 |
| APPLICATION NO. | : 12/196116 | |
| DATED | : March 29, 2011 | |
| INVENTOR(S) | : Sun Wook Hwang, Sang Soo Bang and Sang Heon Lee | |

It is certified that error appears in the above-identified patent and that said Letters Patent is hereby corrected as shown below:

Column 31, line 25 (claim 7, line 2 of subparagraph 1), "treating the transformant;" should be replaced with --containing polynucleotide encoding TRPV2;--.

This certificate supersedes the Certificate of Correction issued May 31, 2011.

Signed and Sealed this
Twenty-eighth Day of June, 2011

David J. Kappos
*Director of the United States Patent and Trademark Office*

SEQUENCE LISTING

```
<160> NUMBER OF SEQ ID NOS: 6

<210> SEQ ID NO 1
<211> LENGTH: 2847
<212> TYPE: DNA
<213> ORGANISM: Artificial Sequence
<220> FEATURE:
<223> OTHER INFORMATION: Synthetic construct:  rTRPV1

<400> SEQUENCE: 1
cagctccaag gcacttgctc catttggggt gtgcctgcac ctagctggtt gcaaattggg        60
ccacagagga tctggaaagg atggaacaac gggctagctt agactcagag gagtctgagt       120
ccccacccca agagaactcc tgcctggacc ctccagacag agaccctaac tgcaagccac       180
ctccagtcaa gccccacatc ttcactacca ggagtcgtac ccggcttttt gggaagggtg       240
```

```
actcggagga ggcctctccc ctggactgcc cttatgagga aggcgggctg gcttcctgcc    300
ctatcatcac tgtcagctct gttctaacta tccagaggcc tggggatgga cctgccagtg    360
tcaggccgtc atcccaggac tccgtctccg ctggtgagaa gcccccgagg ctctatgatc    420
gcaggagcat cttcgatgct gtggctcaga gtaactgcca ggagctggag agcctgctgc    480
ccttcctgca gaggagcaag aagcgcctga ctgacagcga gttcaaagac ccagagacag    540
gaaagacctg tctgctaaaa gccatgctca atctgcacaa tgggcagaat gacaccatcg    600
ctctgctcct ggacgttgcc cggaagacag acagcctgaa gcagtttgtc aatgccagct    660
acacagacag ctactacaag ggccagacag cactgcacat tgccattgaa cggcggaaca    720
tgacgctggt gaccctcttg gtggagaatg gagcagatgt ccaggctgcg gctaacgggg    780
acttcttcaa gaaaaccaaa gggaggcctg gcttctactt tggtgagctg cccctgtccc    840
tggctgcgtg caccaaccag ctggccattg tgaagttcct gctgcagaac tcctggcagc    900
ctgcagacat cagcgcccgg gactcagtgg gcaaacggtt gcttcatgcc ctggtggagg    960
tggcagataa cacagttgac aacaccaagt tcgtgacaag catgtacaac gagatcttga   1020
tcctgggggc caaactccac cccacgctga agctggaaga tcaccaac aggaaggggc    1080 tcacgccact ggctctggct gctagcagtg ggaagatcgg ggtcttggcc tacattctcc   1140
agagggagat ccatgaaccc gagtgccgac acctatccag gaagttcacc gaatgggcct   1200
atgggccagt gcactcctcc ctttatgacc tgtcctgcat tgacacctgt gaaaagaact   1260
cggttctgga ggtgatcgct tacagcagca gtgagacccc taaccgtcat gacatgcttc   1320
tcgtggaacc cttgaaccga ctcctacagg acaagtggga cagatttgtc aagcgcatct   1380
tctacttcaa cttcttcgtc tactgcttgt atatgatcat cttcaccgcg gctgcctact   1440
atcggcctgt ggaaggcttg ccccctata agctgaaaaa caccgttggg gactatttcc   1500
gagtcaccgg agagatcttg tctgtgtcag gaggagtcta cttcttcttc cgagggattc   1560
aatatttcct gcagaggcga ccatccctca agagtttgtt tgtggacagc tacagtgaga   1620 tactttttctt tgtacagtcg ctgttcatgc tggtgtctgt ggtactgtac ttcagccaac   1680
gcaaggagta tgtggcttcc atggtgttct ccctggccat gggctggacc aacatgctct   1740
actatacccg aggattccag cagatgggca tctatgctgt catgattgag aagatgatcc   1800
tcagagacct gtgccggttt atgttcgtct acctcgtgtt cttgtttgga ttttccacag   1860
ctgtggtgac actgattgag gatgggaaga ataactctct gcctatggag tccacaccac   1920
acaagtgccg ggggtctgcc tgcaagccag gtaactctta caacagcctg tattccacat   1980
gtctggagct gttcaagttc accatcggca tgggcgacct ggagttcact gagaactacg   2040
acttcaaggc tgtcttcatc atcctgttac tggcctatgt gattctcacc tacatccttc   2100
tgctcaacat gctcattgct ctcatgggtg agaccgtcaa caagattgca caagagagca   2160
agaacatctg gaagctgcag agagccatca ccatcctgga tacagagaag agcttcctga   2220
agtgcatgag gaaggcgttc cgctctggca agctgctgca ggtggggttc actcctgacg   2280
gcaaggatga ctaccggtgg tgtttcaggg tggacgaggt aaactggact acctggaaca   2340
ccaatgtggg tatcatcaac gaggacccag gcaactgtga gggcgtcaag cgcacccctga   2400 gcttctcect gaggtcaggc cgagtttcag ggagaaactg gaagaacttt gccctggttc   2460
cccttctgag ggatgcaagc actcgagata gacatgccac ccagcaggaa gaagttcaac   2520
tgaagcatta tacgggatcc cttaagccag aggatgctga ggttttcaag gattccatgg   2580
tcccagggga gaaataatgg acactatgca gggatcaatg cggggtcttt gggtggtctg   2640
```

| | |
|---|---|
| cttagggaac cagcagggtt gacgttatct gggtccactc tgtgcctgcc taggcacatt | 2700 |
| cctaggactt cggcgggcct gctgtgggaa ctggggaggtg tgtgggaatt gagatgtgta | 2760 |
| tccaaccatg atctccaaac atttggcttt caactcttta tggactttat aaacagagt | 2820 |
| gaatggcaaa tctctacttg gacacat | 2847 |

```
<210> SEQ ID NO 2
<211> LENGTH: 2768
<212> TYPE: DNA
<213> ORGANISM: Artificial Sequence
<220> FEATURE:
<223> OTHER INFORMATION: Synthetic construct:   rTRPV2

<400> SEQUENCE: 2
```

| | |
|---|---|
| ctgctctgtc cactgtgtga gacgaacagg tggagggtgg acgacgcaga gaaagctcgg | 60 |
| agcgggccgc ggaggttccc acagccccat tactgtcagc gttgagccgc accctccgg | 120 |
| gccgcacttc ctctctcagt ccccgctgcc ggagagcccc gctaggctcg gtgatcctag | 180 |
| cctgcagttt gccgccgcta ccttggct tcagcctgcg ggcccctctc catcaccttc | 240 |
| tccaggtccc agccaggcct gcccctgcgg tatgagagag gaaccttaac atctccatct | 300 |
| ctacagaggt ttcagctgta aggagcatcc tcctctctca ggatgacttc agcctccagc | 360 |
| cccccagctt tcaggctgga gacttccgat ggagatgaag agggcaatgc tgaggtgaac | 420 |
| aaggggaagc aggaaccgcc ccccatggag tcaccattcc agggggagga ccggaattcc | 480 |
| tcccctcaga tcaaagtgaa cctcaacttc ataaagagac ctcctaaaaa cacttctgct | 540 |
| cccagccagc aggagccaga tcggtttgac cgtgaccgac tcttcagtgt ggtctcccgg | 600 |
| ggtgtccccg aggaactgac tggactgcta gaatacctgc gctggaacag caagtacctc | 660 |
| actgactctg catacacaga aggctccact ggaaagacgt gcctgatgaa ggctgtgctg | 720 |
| aaccttcagg atggggtcaa tgcctgcatc atgccgctgc tgcagattga caaggattcc | 780 |
| ggcaatccca gcccctcgt caatgcccag tgcatcgatg agttctacca aggccacagt | 840 |
| gcgctgcaca tcgccataga aagaggagc ctgcagtgcg tgaagctgct ggtagagaat | 900 |
| ggagcggatg ttcacctccg agcctgtggc cgcttcttcc aaaagcacca aggaacttgt | 960 |
| ttctattttg gagagctacc tcttttctctg gctgcgtgca ccaagcagtg ggatgtggtg | 1020 |
| acctacctcc tggagaaccc acaccagccg gccagcctgg aggccaccga ctccctgggc | 1080 |
| aacacagtcc tgcatgctct ggtaatgatt gcagataact cgcctgagaa cagtgccctg | 1140 |
| gtgatccaca tgtacgacgg gcttctacaa atggggggcgc gcctctgccc cactgtgcag | 1200 |
| cttgaggaaa tctccaacca ccaaggcctc acacccctga actagccgc caaggaaggc | 1260 |
| aaaatcgaga ttttcaggca cattctgcag cgggaattct caggaccgta ccagcccctt | 1320 |
| tcccgaaagt ttactgagtg gtgttacggt cctgtgcggg tatcgctgta cgacctgtcc | 1380 |
| tctgtggaca gctgggaaaa gaactcggtg ctggagatca tcgcttttca ttgcaagagc | 1440 |
| ccgaaccggc accgcatggt ggttttagaa ccactgaaca agcttctgca ggagaaatgg | 1500 |
| gatcggctcg tctcaagatt cttcttcaac ttcgcctgct acttggtcta catgttcatc | 1560 |
| ttcaccgtcg ttgcctacca ccagccttcc ctggatcagc cagccatccc ctcatcaaaa | 1620 |
| gcgactttg gggaatccat gctgctgctg ggccacattc tgatcctgct tggggggtatt | 1680 |
| tacctcttac tgggccagct gtggtacttt tggcggcggc gcctgttcat ctggatctca | 1740 |
| ttcatggaca gctactttga aatcctcttt ctccttcagg ctctgctcac agtgctgtcc | 1800 |
| caggtgctgc gcttcatgga gactgaatgg taacctacccc tgctagtgtt atccctagtg | 1860 |

```
ctgggctggc tgaacctgct ttactacaca cggggctttc agcacacagg catctacagt    1920
gtcatgatcc agaaggtcat ccttcgagac ctgctccgtt tcctgctggt ctacctggtc    1980
ttccttttcg gctttgctgt agccctagta agcttgagca gagaggcccg aagtcccaaa    2040
gcccctgaag ataacaactc cacagtgacg gaacagccca cggtgggcca ggaggaggag    2100
ccagctccat atcggagcat tctggatgcc tccctagagc tgttcaagtt caccattggt    2160 atggggagc tggcttttcca ggaacagctg cgttttcgtg gggtggtcct gctgttgctg    2220
ttggcctacg tccttctcac ctacgtcctg ctgctcaaca tgctcattgc tctcatgagc    2280
gaaactgtca ccacgttgc tgacaacagc tggagcatct ggaagttgca gaaagccatc    2340
tctgtcttgg agatggagaa tggttactgg tggtgccgga ggaagaaaca tcgtgaaggg    2400
aggctgctga agtcggcac cagggggat ggtaccccctg atgagcgctg gtgcttcagg    2460
gtggaggaag taaattgggt tgcttgggag aagactcttc ccaccttatc tgaggatcca    2520
tcagggccag gcatcactgg taataaaaag aacccaacct ctaaaccggg gaagaacagt    2580
gcctcagagg aagaccatct gccccttcag gtcctccagt cccctgatg gcccagatgc    2640 agcagcaggc tggcaggatg gagtaggaa tcttcccagc cacaccagag gctactgagt    2700
tttggtggaa atataaatat tttttttgcat aaccaaaaaa aaaaaaaaa aaaaaaaaa    2760 aaaaaagg                                                              2768

<210> SEQ ID NO 3
<211> LENGTH: 2440
<212> TYPE: DNA
<213> ORGANISM: Artificial Sequence
<220> FEATURE:
<223> OTHER INFORMATION: Synthetic construct:  mTRPV3

<400> SEQUENCE: 3
gatctcaagg caaggactgc caccaccatc tggaacctgc cagcatatgc cttaggctcc      60
agcaatgaat gcccactcca aggagatggt gccctcatg ggcaaaagaa ccacggcacc     120
tggcgggaac cctgttgtac tgacagagaa gaggccagca gatctcaccc ccaccaagaa     180
gagtgcacac ttcttcctgg agatagaagg attgagccc aacccacgg tcaccaagac     240 ctctccaccc atcttctcca gccgatgga ctccaacatc cggcagtgcc tctctggcaa     300
ctgtgatgac atggactctc cccagtctcc tcaggatgat gtgacagaga ccccatccaa     360
tcccaacagt ccgagcgcaa acctggccaa ggaagaacag aggcagaaga agaagcgact     420
gaagaagcgc atcttcgcgg ctgtgtccga gggctgcgtg gaggagctgc gggaactcct     480
acaggatctg caggacctct gcaggaggcg ccgcggcctg gatgtgcctg acttcctcat     540
gcacaagctg acagcctcag acaccggaa gacctgcctg atgaaggctt tgctcaacat     600
caatcccaac accaaagaga tcgtgcggat tctgcttgcc ttcgctgagg agaacgacat     660
cctggacagt tcatcaacg ctgagtacac ggaagaggcc tatgaaggc agacagcgct     720 gaacatcgcc atcgagcgc gccagggaga catcacagca gtgcttatag cagcgggtgc     780
tgacgtcaat gctcacgcca agggggtctt cttcaacccc aaataccagc atgaaggctt     840
ctattttggc gagacacccc tggctttggc agcgtgtact aaccagcctg agattgtgca     900
gctgctgatg gagaatgagc agacagacat cacttcccag gattcccggg aaacaacat     960 cctgcacgcg ctggtgacag tggctgagga cttcaagact cagaatgact tcgttaagcg    1020
catgtatgac atgatcctgc tgaggagtgg caactgggag ctgagaccca tgcgcaacaa    1080
cgatgggctc acaccactgc agctggctgc caagatgggc aaggctgaga tcctgaagta    1140
```

-continued

| | |
|---|---|
| catcctcagc cgcgagatca aggagaagcc tctccggagc ttgtccagga agttcacgga | 1200 |
| ctgggcgtat gggcctgtgt catcctcact ctatgacctc accaatgtag acacaacgac | 1260 |
| ggataactct gtgctggaaa tcatcgtcta caacaccaac attgataacc gacatgagat | 1320 |
| gctgaccctg gagcctctgc atacgctgct acacacgaaa tggaagaaat tgccaagta | 1380 |
| catgttcttc ttgtccttct gcttctattt cttctacaac atcaccctga cccttgtctc | 1440 |
| ttactaccgt cctcgggaag atgaggatct cccacacccc ttggccctga cacacaaaat | 1500 |
| gagttggctt cagctcctag ggaggatgtt tgtcctcatc tgggccacat gcatctctgt | 1560 |
| gaaagaaggc attgccattt tcctgctgag accctccgat cttcagtcca tcctgtcaga | 1620 |
| tgcctggttt cactttgtct tttttgtcca agctgtactt gtgatactgt ctgtattctt | 1680 |
| gtacttgttt gcctacaaag aatacctcgc ctgcctcgtg ctggccatgg ccctgggctg | 1740 |
| ggcgaacatg ctctactaca cgagaggctt ccagtctatg ggcatgtaca gcgtcatgat | 1800 |
| ccagaaggtc attttgcatg atgtcctcaa gttcttgttt gtttacatcc tgttcttact | 1860 |
| tggatttgga gtagcgctgg cctcactgat tgagaagtgc tccaaggaca aaaaggactg | 1920 |
| cagttcctat ggcagcttca cgacgcgggc tggagctc ttcaagctca ccataggcct | 1980 |
| gggcgacctg aacatccagc agaactccac ctaccccatc ctctttctct tcctactcat | 2040 |
| cacctatgtc atcctcacct tcgtcctcct cctcaacatg ctcatcgccc tgatggggga | 2100 |
| gacggtggag aacgtctcca agaaagtga gcggatctgg cgcttgcaga gagccaggac | 2160 |
| catcttggag tttgagaaaa tgttaccaga atggctgaga agcagattcc gcatgggcga | 2220 |
| gctgtgcaaa gtagcagatg aggacttccg gctgtgtctg cggatcaacg aggtgaagtg | 2280 |
| gacggaatgg aaaacacacg tgtccttcct taatgaagac ccgggaccca taagacggac | 2340 |
| agcagattta aacaagattc aagattcttc caggagcaat agcaaaacca ccctctatgc | 2400 |
| gtttgatgaa ttagatgaat cccagaaac gtcggtgtag | 2440 |

<210> SEQ ID NO 4
<211> LENGTH: 3211
<212> TYPE: DNA
<213> ORGANISM: Artificial Sequence
<220> FEATURE:
<223> OTHER INFORMATION: Synthetic construct: rTRPV4

<400> SEQUENCE: 4

| | |
|---|---|
| gggaggagga cgcggcggga tcaggaagcg gctgcgctgc gcccgcgtcc caagcaggcc | 60 |
| gagaagtcca acagatctg ctcagggtcc agtatggcag atcctggtga tggccccgt | 120 |
| gcagcgcctg gggatgtggc tgagccccct ggagacgaga gtggcacttc tggtggggag | 180 |
| gccttccccc tctcttccct ggccaacctg tttgagggag aggaaggctc ctcttctctt | 240 |
| tcaccagtgg atgctagccg ccctgctggc cccggggatg gacgtccaaa cctgcgtatg | 300 |
| aagttccagg gcgctttccg caaggggtt cccaacccca ttgacctgct ggagtccacc | 360 |
| ctgtatgagt cctcagtagt gcctgggccc aagaaagcgc ccatggattc gttgttcgac | 420 |
| tatggcactt accggcacca ccccagtgac aacaagagat ggaggaggaa ggtcgtagag | 480 |
| aagcagccac agagcccaa agctcccgcc cccagccac cccccatcct caaagtcttc | 540 |
| aaccggccca tcctctttga catcgtgtcc cggggctcca ctgccgacct ggacggactg | 600 |
| ctctcctact gctgaccca caagaagcgc ctgactgatg aggagttccg ggaaccatcc | 660 |
| acagggaaga cctgcctgcc caaggcactt ctgaacttaa gcaatggccg aaacgacacc | 720 |
| atcccagtgt tgctggacat tgcggaacgc acgggcaaca tgcgggagtt catcaactcg | 780 |

```
cccttcagag acatctacta ccgagggcag acggcactgc acatcgccat tgaacggcgc    840
tgcaagcatt acgtggagct cctggtggcc cagggagccg atgtgcacgc gcaggcccga    900
gggcggttct tccagcccaa ggatgagggt ggctacttct actttgggga gctgcccttg    960
tccttggcag cctgcaccaa ccagccgcac atcgtcaact acctgacaga gaaccctcac   1020
aagaaagccg atatgaggcg acaggactcc agaggcaaca cggtgctcca cgcgctggtg   1080
gccatcgctg caacacccg agagaacacc aagtttgtca ccaagatgta tgacctgttg   1140
cttctcaagt gctcccgcct cttcccagac agcaacctgg agactgtgct aacaatgac    1200
ggtctttcgc ccctcatgat ggctgccaag actggcaaga tcgggtcttt tcagcacatc   1260
atccgacggg aggtgacaga tgaggacaca cggcacctgt ctcgcaagtt caaggactgg   1320
gcctacgggc ctgtgtattc ttctctctac gacctctcct ccctggatac gtgcggggag   1380
gaagtgtccg tgctggagat cctggtttac aacagcaaga tcgagaaccg ccatgagatg   1440
ctggctgtgg agcccattaa cgaactgctg agggacaagt ggcgtaagtt cggggccgtg   1500
tccttctaca tcaacgttgt ctcctatctg tgtgccatgg tcatcttcac cctcacagcc   1560
tactatcagc cactggaggg cacgccaccc tacccttacc gtaccacggt ggactacctg   1620
aggctggctg gtgaggtcat cacgctcctc acaggagtcc tgttcttctt taccagtatc   1680
aaagacttgt tcatgaagaa atgccctgga gtgaattctc tcttcgtcga tggctccttc   1740
cagttgctct acttcatcta tcagtgctg gtggttgtgt ctgcggcgct ctacctggca   1800
gggatcgagg cctatctggc tgtgatggtc tttgccctgg tcctgggctg gatgaatgcc   1860
ctttacttca cccgtgggct gaagctgaca gggacctaca gcatcatgat tcagaagatc   1920
ctcttcaaag atctcttccg ctttctgctg gtctacctgc tttttatgat tggctatgcc   1980
tcagctctgg tcaccctcct gaatccgtgc accaacatga aggtctgtaa cgaggaccag   2040
agcaactgca cggtgccctc ataccccgcg tgccggaca gcgagacctt cagcgccttc   2100
ctactggacc tcttcaagct caccatcggc atgggcgacc tggagatgct gagcagcgct   2160
aagtaccccg tggtcttcat tctcctgctg gttacctaca tcatcctcac cttcgtgctc   2220
ctgctgaaca tgctcatcgc cctcatgggt gagaccgtgg ccaggtgtc caaggagagc   2280
aagcacatct ggaagctgca gtgggccacc accatcctgg acatcgagcg ctccttccct   2340
gtgttcctga ggaaggcctt ccgctccgga gagatggtga cagtgggcaa gagctcggat   2400
ggcactccag accgcaggtg gtgcttcagg gtggacgagg tgaactggtc tcactggaac   2460
cagaacctgg gcatcattaa cgaggacccc ggcaagagcg agatctacca gtactatggc   2520
ttctcccata ccatggggcg cctccgcagg atcgctggt cctcagtggt gccccgcgtg   2580
gtggagctga acaagaactc aggcacagat gaagtggtgg tcccccctgga taacctaggg   2640
aaccccaact gtgacggcca ccagcaaggt tatgctccca gtggagggc ggaggacgca   2700
ccactgtagg ggccatgcca gggctgggt caatggccca ggcttggccc ttgctcccac   2760
ctacatttca gcatctgtcc tgtgtcttcc cacacccaca cgtgacctcg gaggtgaggg   2820
cctctgtgga gactctgggg aggccccagg accctctggt ccccacaaag acttttgctc   2880
ttatttctac tcctccccac atgggggacg gggctcctgg ccacctgtct cactcccatg   2940
gagtcaccta agccagctca gggccctcc actcacaggg ctcaggcccc tgtccctctt   3000
gtgcactatt tattgctctc ctcaggaaaa tgacatcaca ggagtctacc tgcagctgga   3060
acctggccag ggctgaggct catgcaggga cactgcagcc ctgacccgct gcagatctga   3120
```

```
cctgctgcag cccgggctag ggtgggtctt ctgtactttg tagagatcgg ggctgttggt    3180
gctcaataaa tgtttgttta ttctcggtgg a                                   3211

<210> SEQ ID NO 5
<211> LENGTH: 3869
<212> TYPE: DNA
<213> ORGANISM: Artificial Sequence
<220> FEATURE:
<223> OTHER INFORMATION: Synthetic construct:  mTRPM8

<400> SEQUENCE: 5
tcctccctcc tccagtgagc taagagacaa gcaggctctt tgaggagaga gaagctcttg      60
gctgattgag cagctccacg tcctggctgt cccggagctt gatacataga aaagactgac     120
ctcagataca cagagatcct tctgcttctg tctcccaagt gctgggatca caggcaagat     180
gtccttcgag ggagccaggc tcagcatgag gagccgcaga aatggtacta tgggcagcac     240
ccggaccctg tactccagtg tatctcggag cacagacgtg tcctacagtg acagtgattt     300
ggtgaatttt attcaggcaa attttaaaaa acgagaatgt gtcttcttta ccagagactc     360
caaggccatg gagaacatat gcaagtgtgg ttatgcccag agccagcaca tcgaaggcac     420
ccagatcaac caaaatgaga gtggaactaa caaaaacat accaaggagt tccaacaga     480 cgccttcggg gacattcagt ttgagactct ggggaagaaa ggcaagtact tacgcttgtc     540
ctgtgacacc gactctgaaa ctctctacga actgctgacc cagcactggc acctcaaaac     600
acccaacctg gtcatttcag tgacgggtgg agccaaaaac tttgctttga agccacgcat     660
gcgcaagatc ttcagcaggc tgatttacat cgcacagtct aaaggtgcgt ggattctcac     720
tggaggcact cactacggcc tgatgaagta cataggcgag gtggtgagag acaacaccat     780
cagcaggaac tcagaagaga catcgtggcc cattggcatc gcagcatggg gcatggtctc     840
caacagggac accctcatca ggagctgtga tgatgaggga catttttcag ctcaatacat     900
catggatgac tttaccagag accctctata catcctggac aacaaccata cccacctgct     960
gcttgtggac aacggttgtc atggacaccc cacagtggaa gccaagctcc ggaatcagct    1020
ggaaaagtac atctctgagc gcaccagtca agattccaac tatggtggta agatccccat    1080
cgtgtgtttt gcccaaggag gtggaagaga gactctaaaa gccatcaaca cctctgtcaa    1140
aagcaagatc ccttgtgtgg tggtggaagg ctcggggcag attgctgatg tgatcgccag    1200
cctggtggag gtggaggatg tttttaacct cttccatggt c aaagagaagc tggtacgctt    1260
tttaccacgc actgtgtccc ggctgcctga agaggaaatt gagagctgga tcaaatggct    1320
caaagaaatt cttgagagtt ctcacctact cacagtaatt aagatggaag aggctggaga    1380
tgagattgtg agcaacgcca tttcctatgc gctgtacaaa gccttcagca ctaatgagca    1440
agacaaggac aactggaatg gacagctgaa gcttctgctg gagtggaacc agttggacct    1500
tgccagtgat gagatcttca ccaatgatcg ccgctgggag tctgccgacc ttcaggaggt    1560
catgttcacg gctctcataa aggacagacc caagtttgtc cgcctctttc tggagaatgg    1620
cctgaatctg cagaagtttc tcaccaatga agtcctcaca gagctcttct ccacccactt    1680
cagcacccta gtgtaccgga atctgcagat cgccaagaac tcctacaatg acgcactcct    1740
cacctttgtc tggaagttgg tggcaaactt ccgtcgaagc ttctggaaag aggacagaag    1800
cagcagggag gacttggatg tggaactcca tgatgcatct ctcaccaccc ggcacccgct    1860
gcaagctctc ttcatctggg ccattctttc gaacaagaag gaactctcca aggtcatttg    1920
ggagcagacc aaaggctgta ctctggcagc cttgggggcc agcaagcttc tgaagaccct    1980
```

| | |
|---|---|
| ggccaaagtt aagaatgata tcaacgctgc tggggaatcg gaggaactgg ccaatgaata | 2040 |
| tgagacccga gcagtggagt tgttcaccga gtgttacagc aatgatgaag acttggcaga | 2100 |
| acagctactg gtctactcct gcgaagcctg gggtgggagc aactgtctgg agctggcagt | 2160 |
| ggaggctaca gatcagcatt tcatcgctca gcctggggtc cagaatttcc tttctaagca | 2220 |
| atggtatgga gagatttccc gagacacgaa gaactggaag attatcctgt gtctattcat | 2280 |
| catcccctta gtgggctgtg gcctcgtatc atttaggaag aaacccattg acaagcacaa | 2340 |
| gaagctgctg tggtactatg tggccttctt cacgtcgccc ttcgtggtct tctcctggaa | 2400 |
| cgtggtcttc tacatcgcct tcctcctgct gtttgcctat gtgctgctca tggacttcca | 2460 |
| ctcagtgcca cacacccccg agctgatcct ctacgccctg gtcttcgtcc tcttctgtga | 2520 |
| tgaagtgagg cagtggtaca tgaacggagt gaattatttc accgacctat ggaacgttat | 2580 |
| ggacaccctg ggactcttct acttcatagc gggtattgta ttccggctcc actcttctaa | 2640 |
| taaaagctcg ttgtactctg gcgcgtcat tttctgtctg gattacatta tattcacgct | 2700 |
| aaggctcatc cacattttca ccgtcagcag gaacttggga cccaagatta taatgctgca | 2760 |
| gcggatgctg atcgacgttt tcttcttcct gttcctcttt gctgtgtgga tggtggcctt | 2820 |
| tggcgtggcc agacagggga tcctaaggca aaatgaacag cgctggagat ggatcttccg | 2880 |
| ctctgtcatc tatgagccct acctggccat gtttggccag gttcccagtg acgtggatag | 2940 |
| taccacatat gacttctccc actgtacctt ctcgggaaat gagtccaagc cactgtgtgt | 3000 |
| ggagctggat gagcacaacc tgccccgctt ccctgagtgg atcaccattc cgctggtgtg | 3060 |
| catctacatg ctctccacca atatccttct ggtcaacctc ctggtcgcca tgtttggcta | 3120 |
| cacggtaggc attgtacagg agaacaacga ccaggtctgg aaattccagc ggtacttcct | 3180 |
| ggtgcaggag tactgcaacc gcctaaacat cccccttccc ttcgttgtct tcgcttattt | 3240 |
| ctacatggtg gtgaagaagt gttttcaaatg ctgctgtaaa gagaagaata tggagtctaa | 3300 |
| tgcctgctgt ttcagaaatg aggacaatga actttggcg tgggagggtg tcatgaagga | 3360 |
| gaattacctt gtcaagatca acacgaaagc caacgacaac tcagaggaga tgaggcatcg | 3420 |
| gtttagacaa ctggactcaa agcttaacga cctcaaaagt cttctgaaag agattgctaa | 3480 |
| taacatcaag taaggctggc gatgcttgtg gggagaaacc aaatcacaat gaggtcacag | 3540 |
| caaccacctg gatgtggagg ctcatgggac actgatggac agtactgcta atgacttcta | 3600 |
| aaggagacat tttcaggtcc ctgagcacag ggtggatgac tcttagtcac cctcaagggc | 3660 |
| ataggtcagg gagcaaagtg tacagaggac tttacacctg aagagggtg caaaggacca | 3720 |
| tgttcttctg tgaaggtgcc tgtgtttttct gcatctcaga gccttgtcct gatgctgagg | 3780 |
| gattaagtgt tgacactcct ttcccacgac tgtgactctg gccctgattt tatacttata | 3840 |
| ctgcaaaaaa aaaaaaaaaa aaaaaaaaa | 3869 |

<210> SEQ ID NO 6
<211> LENGTH: 4263
<212> TYPE: DNA
<213> ORGANISM: Artificial Sequence
<220> FEATURE:
<223> OTHER INFORMATION: Synthetic construct: mTRPA1

<400> SEQUENCE: 6

| | |
|---|---|
| gcgccagccg gcgtccaggt ggagtcaatg aagcgcggct tgaggaggat tctgctcccg | 60 |
| gaggaaagga aggaggtcca gggcgttgtc tatcgcggcg tcgggaaga catggactgc | 120 |
| tccaaggaat cctttaaggt ggacattgaa ggagatatgt gtagattaga agacttcatc | 180 |

```
aagaaccgaa gaaaactaag caaatatgag gatgaaaatc tctgtcctct gcatcacgca    240
gcagcagaag gtcaagttga actgatggaa ctgatcatca atggttcttc gtgtgaagtg    300
ctgaatataa tggatggtta tggaaatacc ccactgcatt gtgctgcaga aaaaaatcaa    360
gttgaaagtg taaagtttct tctcagccaa ggagcaaatc caaacctccg aaatagaaac    420
atgatgtcac cccttcacat agctgtgcat ggcatgtaca acgaagtgat caaggtgttg    480
actgagcaca aggccactaa catcaattta aaggagaga atgggaacac ggctttgatg     540
tccacgtgtg ccaaagacaa cagtgaagct ttgcaaattt tgttagaaaa aggagctaag    600
ctgtgtaaat caaataagtg gggagactac cctgtgcacc aggcagcatt ttcaggtgcc    660
aaaaaatgca tggaattaat cttagcatat ggtgaaaaga acggctacag cagggagact    720
cacattaatt ttgtgaatca caagaaagcc agccctctcc acctagcagt tcaaagcgga    780
gacttggaca tgattaagat gtgcctggac aacggtgcac acatcgacat gatggagaat    840
gccaaatgca tggcccctcca ttttgctgca acccagggag ccactgacat cgttaagctc    900
atgatctcat cctataccgg aagtagtgat attgtgaatg cagttgatgg caatcaggag    960
accctgcttc acagagcctc gttatttgat caccatgacc tggcagaata cctaatatca   1020
gtgggagcag acatcaacag cactgattct gaaggacgct ctccacttat tttagcaaca   1080
gcttctgcat cctggaacat tgtgaatttg ctcctctgta aggtgccaa agtagacata    1140 aaagatcatc ttggacgtaa cttttttgcat ttgactgtgc agcagcctta tggactaaga   1200
aatttgcggc ctgagtttat gcagatgcaa cacatcaaag agctggtgat ggatgaagac   1260
aatgacggat gcacacctct ccattatgcc tgtaggcagg gggttcctgt ctctgtaaat   1320
aacctccttg gcttcaatgt gtccattcat agcaaaagta agataagaa gtcgcccctg    1380 cattttgcag ccagttatgg gcgcatcaat acatgtcaga gacttctgca agacataagt   1440
gatacgaggc ttttgaatga aggggatctc catgggatga cccctctcca cctggcagca   1500
aaaaatgggc atgataaagt cgttcaactc cttctgaaga aaggggcctt atttctcagt   1560
gaccacaatg gctggactgc tttgcatcac gcctccatgg gtgggtacac tcagaccatg   1620
aaggtcattc ttgatactaa cttgaaatgc acagaccgac tagatgaaga agggaacaca   1680
gcactccact ttgcagcacg ggaaggccat gccaaggctg ttgcaatgct ttttgagctac   1740 aatgctgaca tcctcctgaa caagaagcaa gcttcctttc tgcatattgc cctgcacaat   1800
aagcgcaagg aagtggttct cacaaccatc agaaataaaa gatgggatga gtgtcttcaa   1860
gttttcactc ataattctcc aagcaatcga tgtccaatca tggagatggt agaataccctc   1920 cccgagtgca tgaaagttct tttagatttc tgcatgatac cttccacaga agacaagtcc   1980
tgtcaagact accatattga gtataatttc aagtatctcc aatgcccatt atccatgacc   2040
aaaaaagtag cacctaccca ggatgtggta tatgagcctc ttacaatcct caatgtcatg   2100
gtccaacata accgcataga actcctcaac caccctgtgt gtagggagta cttactcatg   2160
aaatggtgtg cctatggatt cagagcccat atgatgaacc taggatctta ttgtcttggt   2220 ctcatacccca tgaccttct tgttgtcaaa atacagcctg gaatggcctt caattctact   2280
ggaataatca atggaactag tagtactcat gaggaaagaa tagacactct gaattcatt    2340 ccaataaaaa tatgtatgat tctagttttt ttatcaagta tatttggata ttgcaaagaa   2400
gtgatccaaa ttttccaaca gaaaaggaat tacttcctgg attacaacaa tgctctggaa   2460
tgggttatct atacaactag tatcatcttc gtgttgccct tgttcctcaa catcccagcg   2520
tatatgcagt ggcaatgtgg agcaatagcg atattcttct actggatgaa cttcctactg   2580
```

```
tatcttcaaa ggtttgagaa ctgtggaatt ttcattgtta tgttggaggt gattttttaaa    2640 acattgctga gatcgaccgg agtgtttatc ttcctcctac tggcttttgg cctcagcttt    2700
tatgttctcc tgaatttcca agatgccttc agcaccccat tgctttcctt aatccagaca    2760
ttcagtatga tgctaggaga catcaattat cgagatgcct tcctagaacc attgtttaga    2820
aatgagttgg catacccagt cctgacctttt gggcagctta ttgccttcac aatgtttgtc    2880
ccaattgttc tcatgaactt actgattggc ttggcggttg gggacattgc tgaggtccag    2940
aagcatgcgt cattgaagag gattgctatg caggtggaac ttcataccaa cttagaaaaa    3000
aagctgccac tctggtactt acgcaaagtg gatcagaggt ccaccatcgt gtatccaaat    3060
agacccaggc acggcaggat gctacggttt tttcattact ttcttaatat gcaagaaaca    3120
cgacaagaag taccaaacat tgacacatgc ttggaaatgg aaatattgaa acagaaatat    3180
cggctgaagg acctcacttc cctcttggaa aagcagcatg agctcatcaa actcatcatc    3240
cagaagatgg agatcatctc agagacagaa gatgaagata accattgctc tttccaagac    3300
aggttcaaga aggagaggct ggaacagatg cacagcaagt ggaattttgt cttaaacgca    3360
gttaagacta aaacacattg ttctattagc cacccggact tttagttctg tgtcttatgg    3420
gagtgggaga ctgctttaca tacttatttc agtgaatttc agtttggaaa agagcaaaga    3480
aacagaaagt tgactaacat tgctgcatgg agatcctagt tcctgcaacc tcacccatac    3540
atatgctcat atttcctgtc aattactatg tattgagaag atcctttctg acatgttcaa    3600
tttgaacatg aaggatagtc tctttcgagt gaataaaaac cagggttgtt ggaatgcata    3660
ttatggagga taagaattaa tgtaactatt aaggcagaac acaactacat aatacaagat    3720
gcatataatt ccaagtatta tatttaatct cctaccatgt taaaccttcc tgtgttataa    3780
cctgtctggg acactataat ctctgttcct actatgatta gatcatagtc tcaccctcct    3840
cgtcccatca cacatgacat cattttgagc cacatgacag aagtcctagt tagtagactg    3900
tgataagtat gaatgttaca atagaaatgt gttcccttag tgttcatcag ttgtgatggt    3960
ttaaatgaga aacgttgccc acagactcat acatttaaac ccttagtccc agttgttgct    4020
gctgcttagg ggggccacac agccttgctt gctctctcct ttctgagtgt ggagagaaat    4080
gtgatcagta agactcctgc tcctgctgcc atgctcttta ttccattatg gacttcttct    4140
gaaactgcaa gcagaaattc actgttcctt cctcaaattt cttttggtca tggtattata    4200
tcatagcaac agaaactaac ttatgtacca atggtcttaa taaagaataa agcctgtaca    4260
gtc                                                                   4263
```